(12) United States Patent　　(10) Patent No.:　US 12,605,687 B2

Shigaki　　(45) Date of Patent:　Apr. 21, 2026

(54) METHANATION REACTION DEVICE USING ENDOTHERMIC REACTION FOR REMOVAL OF REACTION HEAT AND REGENERATION PROCESS FOR HEAT-ABSORBING MATERIAL

(71) Applicant: Yoshiki Shigaki, Nagareyama (JP)

(72) Inventor: Yoshiki Shigaki, Nagareyama (JP)

( * ) Notice: Subject to any disclaimer, the term of this patent is extended or adjusted under 35 U.S.C. 154(b) by 404 days.

(21) Appl. No.: 18/010,800

(22) PCT Filed: Oct. 6, 2021

(86) PCT No.: PCT/JP2021/036892
§ 371 (c)(1),
(2) Date: Dec. 15, 2022

(87) PCT Pub. No.: WO2022/075336
PCT Pub. Date: Apr. 14, 2022

(65) Prior Publication Data
US 2023/0234013 A1　　Jul. 27, 2023

(30) Foreign Application Priority Data

Oct. 9, 2020　(JP) ................................. 2020-171378
Oct. 5, 2021　(JP) ................................. 2021-163778

(51) Int. Cl.
B01J 8/26　　　　(2006.01)
B01J 8/38　　　　(2006.01)
(Continued)

(52) U.S. Cl.
CPC ................. B01J 8/26 (2013.01); B01J 8/388 (2013.01); B01J 23/46 (2013.01); C01F 5/14 (2013.01);
(Continued)

(58) Field of Classification Search
CPC ..... B01J 8/26; B01J 8/388; B01J 23/46; B01J 2219/00058; B01J 2219/185;
(Continued)

(56) References Cited

U.S. PATENT DOCUMENTS

2020/0239381 A1　7/2020　Ahougue

FOREIGN PATENT DOCUMENTS

JP　　　S62-241801 A　　10/1987
JP　　　2016-524796　　　8/2016
(Continued)

OTHER PUBLICATIONS

Chemical Engineering 31 (6), p. 538 (1967), Shiro Maeda, Nerio Yamakawa.

(Continued)

*Primary Examiner* — Kaity V Chandler

(74) *Attorney, Agent, or Firm* — Maschoff Brennan

(57)　　　　　　ABSTRACT

Embodiments of the present disclosure relate to an apparatus capable of removing the reaction heat and lower the reaction temperature as the reaction progresses in order to increase the conversion ratio to methane. In some embodiments, powders of magnesium hydroxide and magnesium carbonate, which are chemical heat storage agents, are used as part of the fluidizing medium of the multi-stage fluidized bed in the temperature range where the methanation reaction proceeds. In some embodiments, the heat generated during the methanation reaction can be absorbed and stored in the powder. In some embodiments, after discharging the magnesium oxide generated by endotherm, the powder can be regenerated with an external regenerating facility and then the storage heat can be released and recovered. The regenerated powder can be fed to the uppermost stage of the
(Continued)

multi-stage fluidized bed at a temperature lower than the internal temperature of the reactor to lower inside temperature.

18 Claims, 8 Drawing Sheets

(51) Int. Cl.
  *B01J 23/46*      (2006.01)
  *C01F 5/14*      (2006.01)
  *C01F 5/24*      (2006.01)
  *C07C 9/04*      (2006.01)

(52) U.S. Cl.
  CPC .................. *C01F 5/24* (2013.01); *C07C 9/04* (2013.01); *B01J 2219/00058* (2013.01); *B01J 2219/185* (2013.01)

(58) Field of Classification Search
  CPC ...... B01J 2208/00017; B01J 8/28; B01J 8/40; B01J 23/462; B01J 23/755; C01F 5/14; C01F 5/24; C01F 5/06; C01F 5/08; C01F 5/16; C07C 9/04; C07C 2521/10; C07C 1/12; B01D 53/83; B01D 2251/402; B01D 2251/604; B01D 2257/504; B01D 2258/0283; B01D 53/62; Y02C 20/40; Y02P 20/133
  See application file for complete search history.

(56)        References Cited

FOREIGN PATENT DOCUMENTS

| | | | |
|---|---|---|---|
| JP | 2020-63206 | | 4/2020 |
| JP | 2020-71387 | | 5/2020 |
| JP | 2020-100597 | A | 7/2020 |
| JP | 2020-163248 | A | 10/2020 |
| WO | 2018/025555 | A1 | 2/2018 |
| WO | 2021/015056 | A1 | 1/2021 |
| WO | 2021/100767 | A1 | 5/2021 |

OTHER PUBLICATIONS

Examples and Issues of Technologies for Chemically Storing Exhaust Heat: Society of Automotive Engineers of Japan No. 14-14 Symposium, Feb. 13, 2015 by Takayuki Kobayashi.
Journal of Ceramic Association of Japan, 71, p. 61, (1963), Kenya Hamano.
Journal of the Chemical Society of Japan, p. 57-64, (1979), Yutaka Sawada, et al.
"Methane Synthesis Test Facility utilizing Carbon Dioxide" https://www.nedo.go.jp/news/press/AA5_101217.html, Oct. 16, 2019, New Energy and Industrial Technology Development Organization (NEDO), Inpexcorporation, and Hitachi Zosen Corporation.
"University of Toyama Hydrogen Isotope Science Research Center Research Report", 36, 39-44, (2016), Abe et al.

[Figure 1]
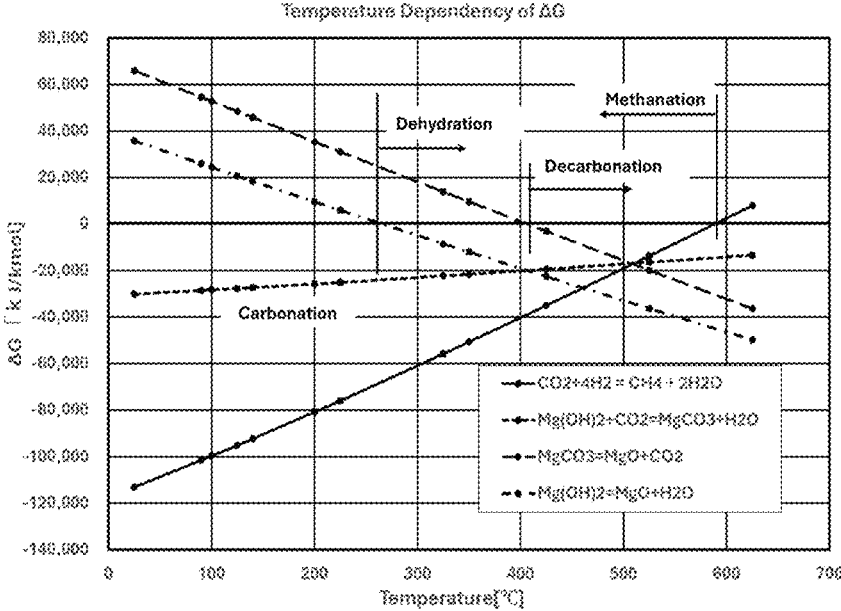
[Figure 2]
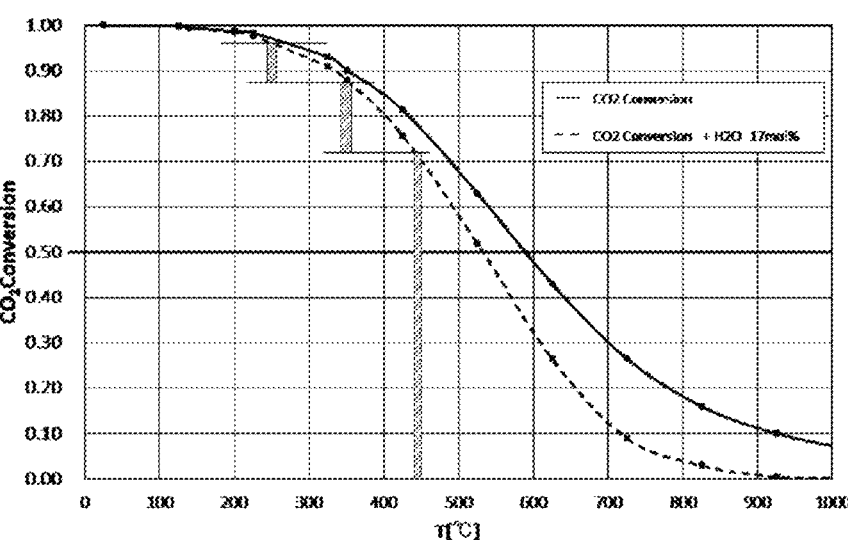
[Figure 3]
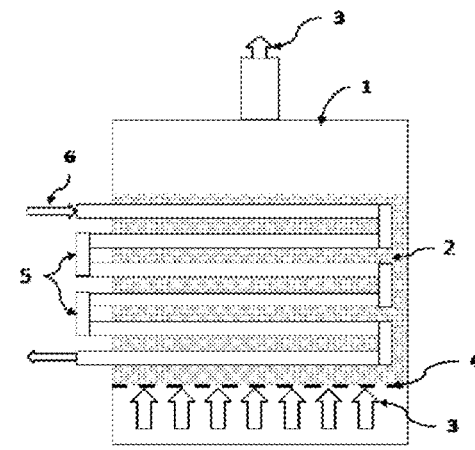

[Figure 4]
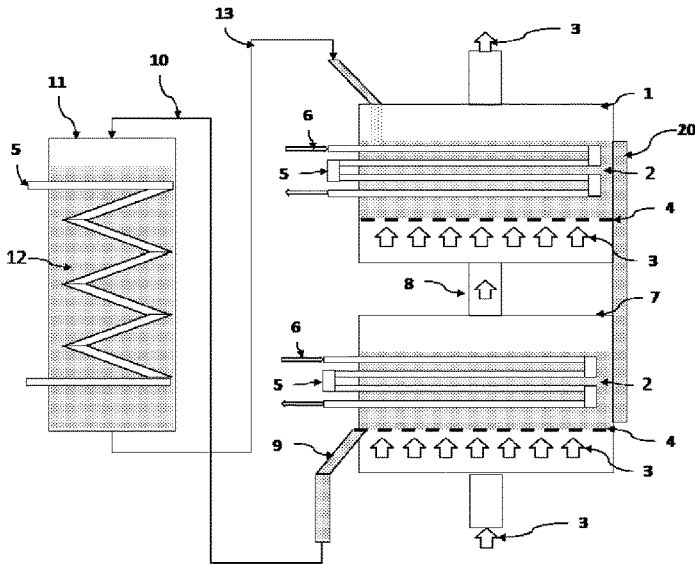
[Figure 5]
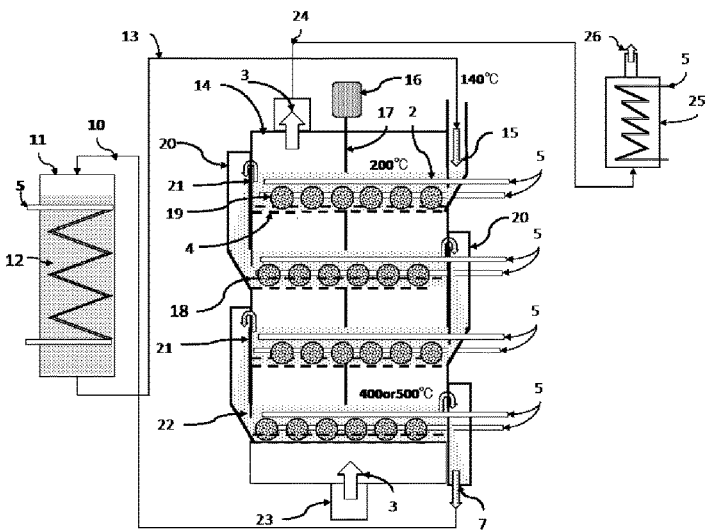
[Figure 6]
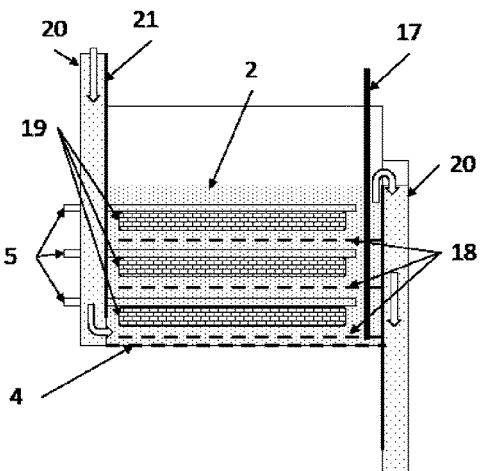

[Figure 7]
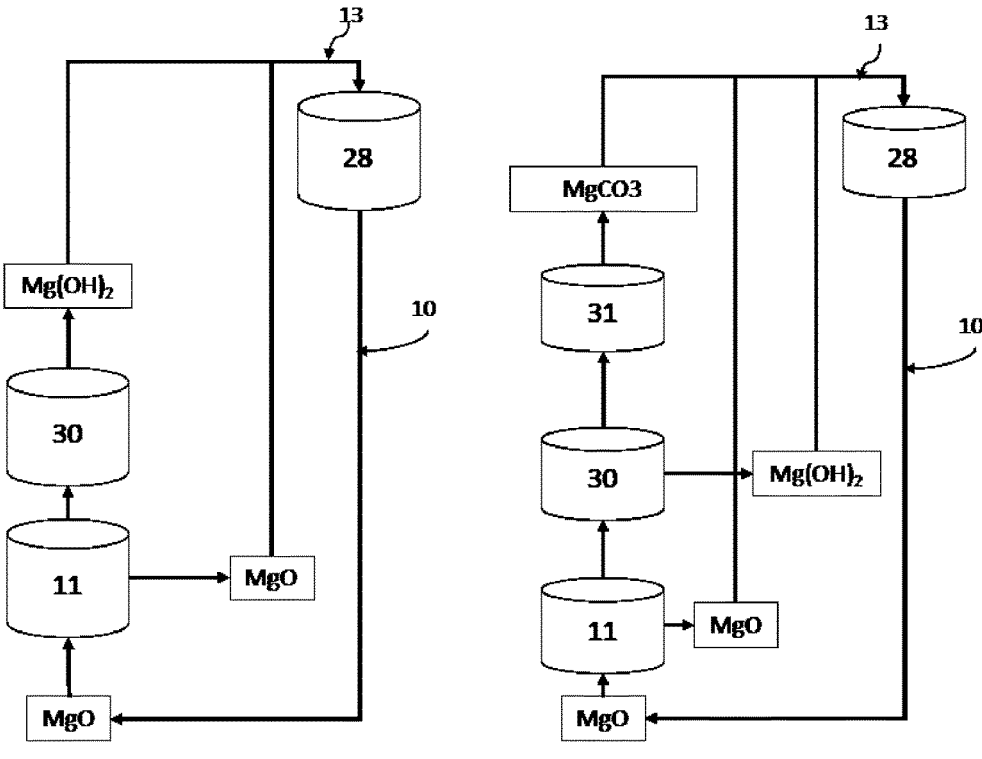
[Figure 8]
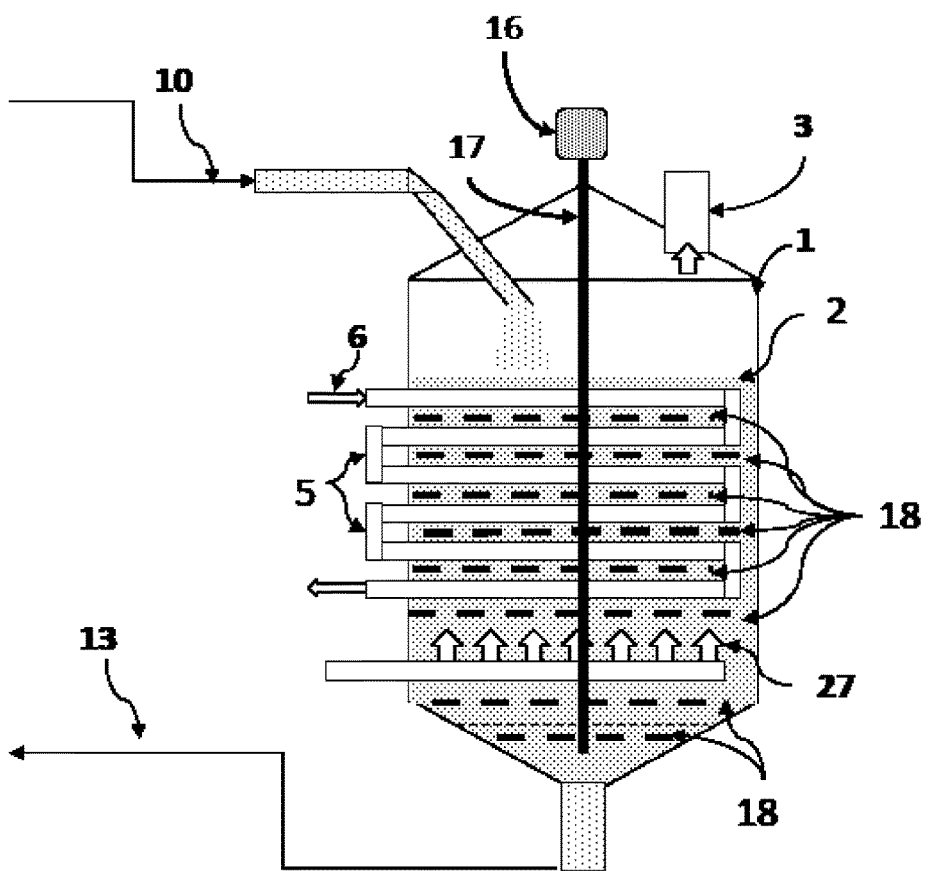

[Figure 9]
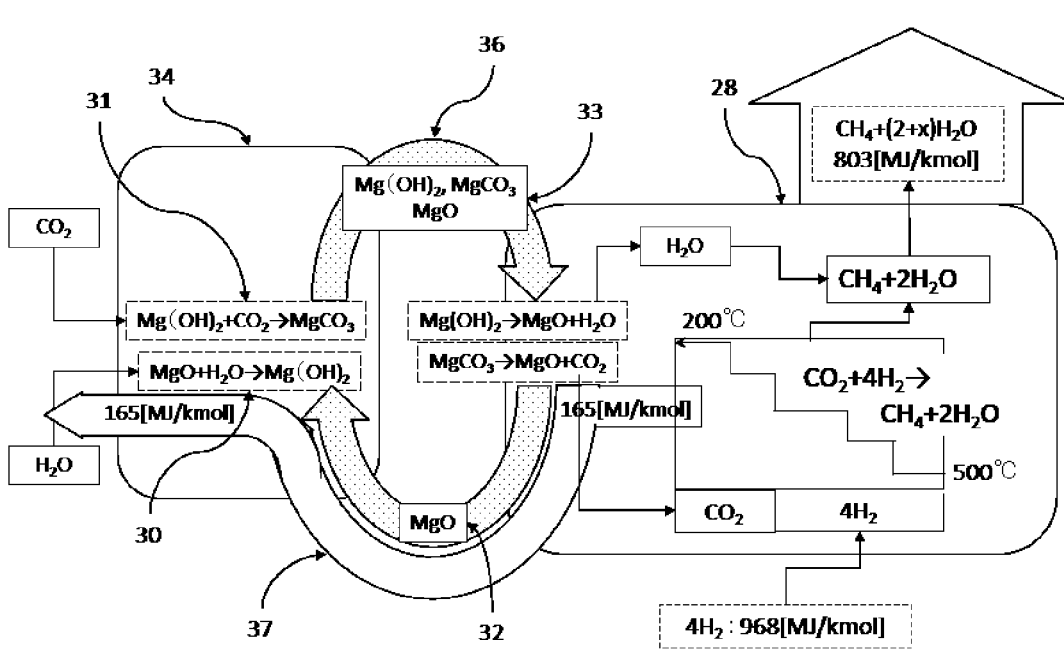
[Figure 10]

[Figure 11]
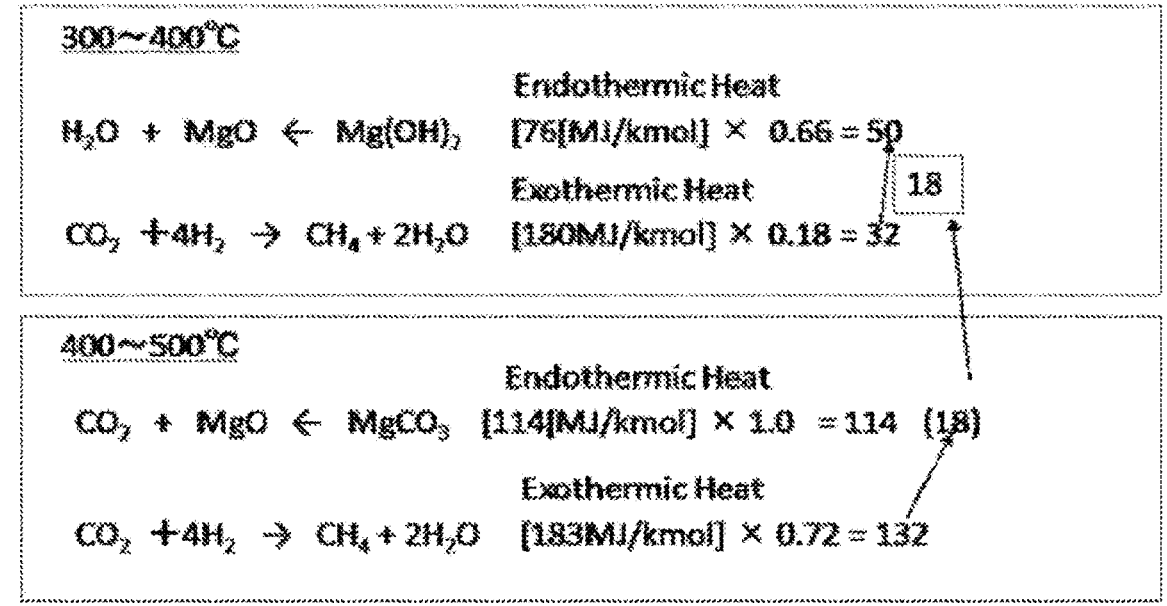
[Figure 12]
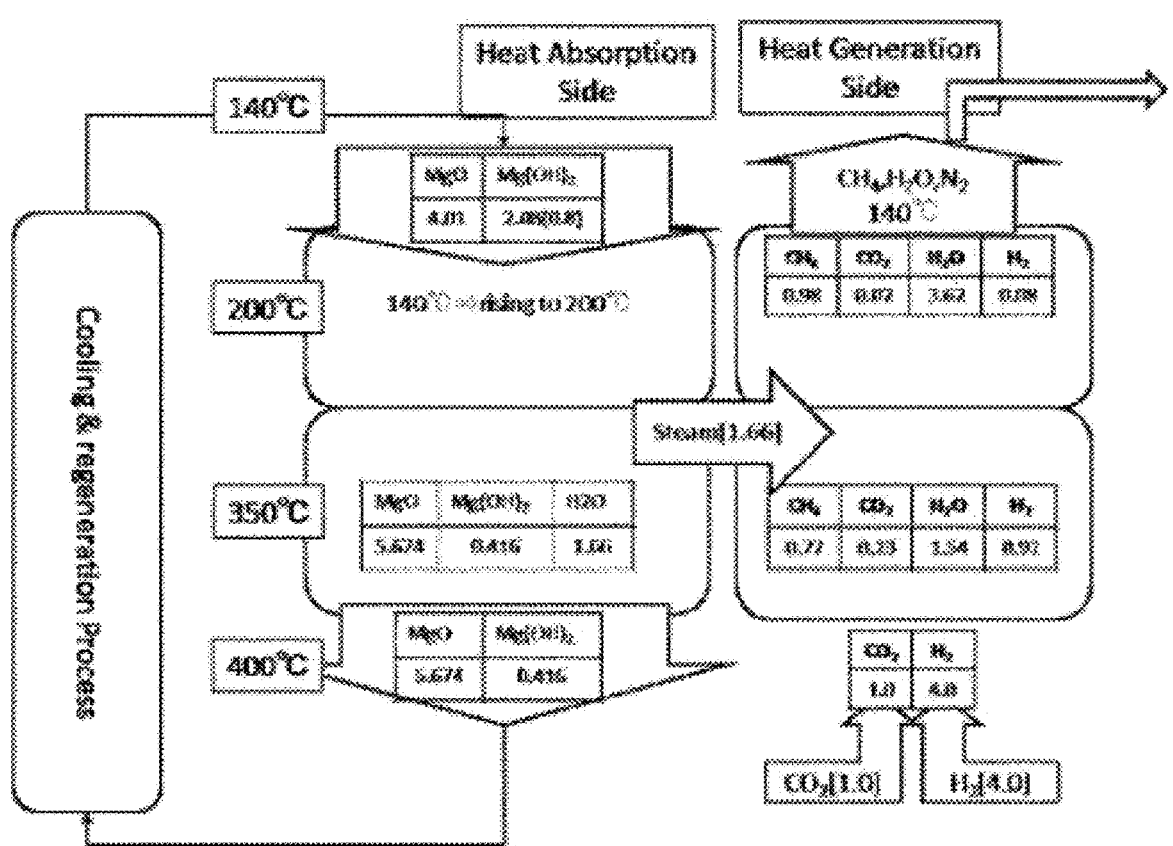

[Figure 13]
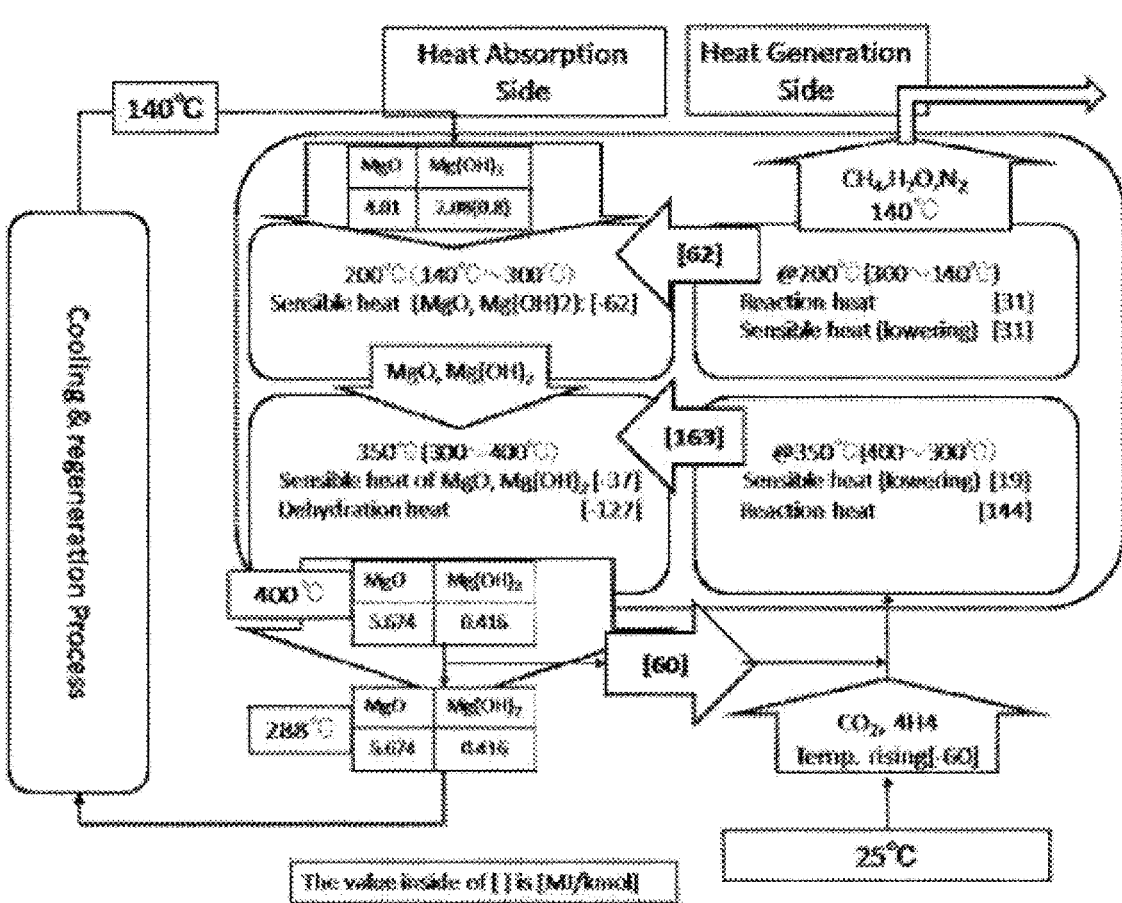

[Figure 14]
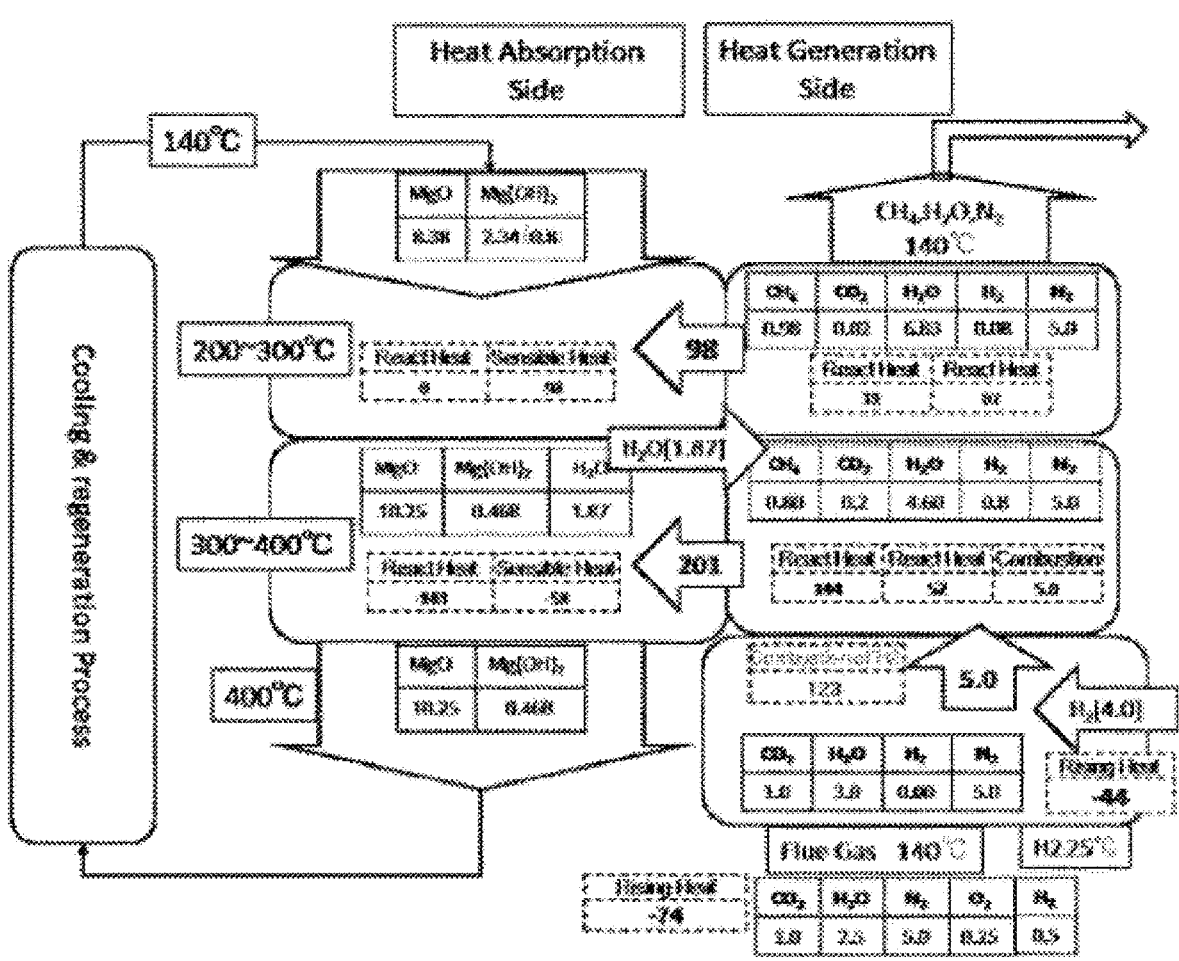

[Figure 15]
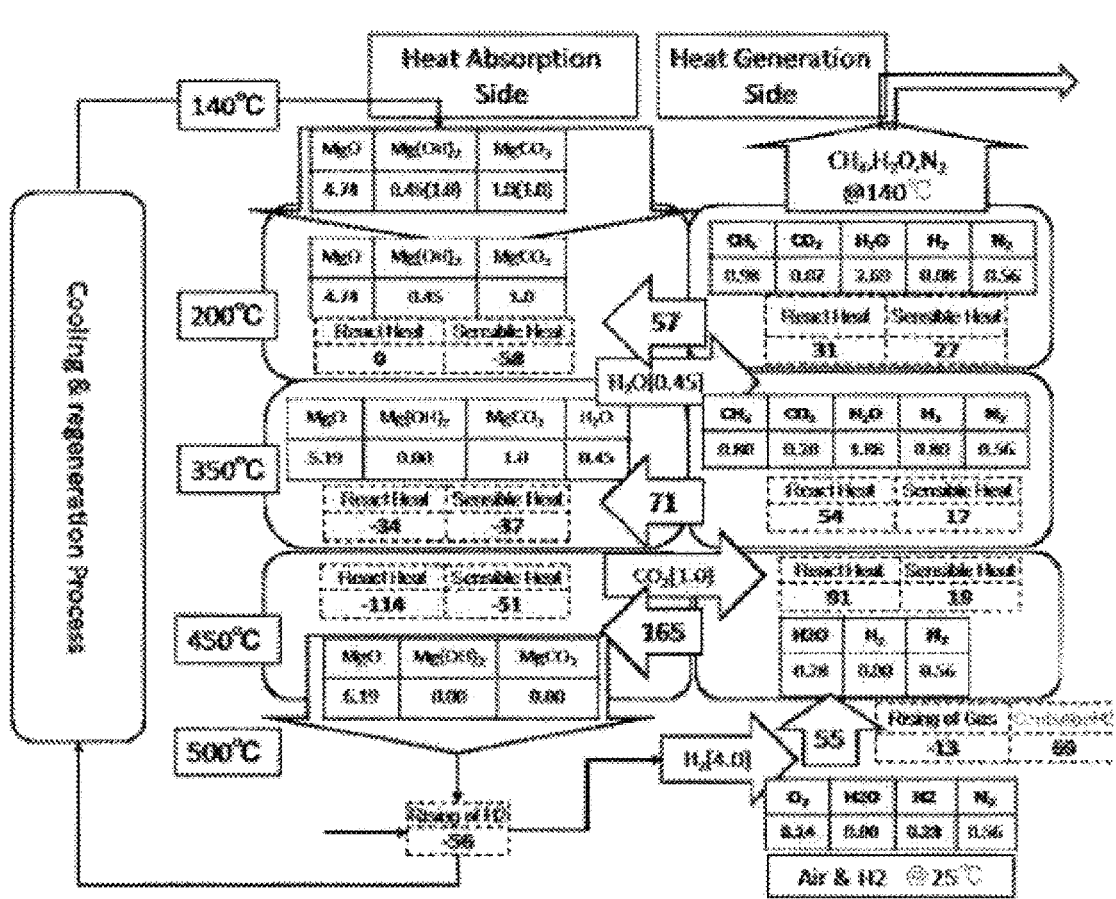

METHANATION REACTION DEVICE USING ENDOTHERMIC REACTION FOR REMOVAL OF REACTION HEAT AND REGENERATION PROCESS FOR HEAT-ABSORBING MATERIAL

TECHNICAL FIELD

In recent years, in order to prevent or reduce the atmospheric concentration of carbon dioxide, which is a global warming gas, CCS, which is a technology for separating and recovering carbon dioxide, and CCUS (Carbon Capture Utilization & Separation) technology, which includes its use, are being developed.

On the other hand, in promoting the use of renewable energies, in order to make fluctuating power such as solar power and wind power a stable energy supply source according to demand, hydrogen (green hydrogen) is produced by electrolysis using these power. And, development and demonstration of the hydrogen conversion process that manufactures, stores and utilizes this hydrogen is also underway Furthermore, a methanation (=methanization reaction) process that converts carbon dioxide captured by the above CCS technology and hydrogen obtained from this renewable energy into methane, which is safer, more compatible with current infrastructure and easier to uses is under developing.

The present invention is relating to CCUS technology that merges the CCS technology that captures carbon dioxide with the process of converting hydrogen into methane.

BACKGROUND TECHNOLOGY

At present, the mainstream of technology for absorbing, separating and recovering carbon dioxide from the atmosphere or flue gas is the absorption method using an amine-based absorbent. There are multiple types of amine absorption liquids to be used, but all of them absorb carbon dioxide in the flue gas in the range of room temperature to 50° C., and then heat it to 100° C. to 150° C. to decarbonate and recover carbon dioxide. In addition, as described in Non-Patent Document 3, a method in which solid particles are impregnated with amine to absorb carbon dioxide is also existed.

On the other hand, according to Non-Patent Document 1, the method of synthesizing methane from hydrogen and carbon dioxide proceeded in the presence of a Ni-based catalyst was discovered by Sabatier about 120 years ago. However, it could not realize as actual mass production process until today. The main reason for this is that this reaction occurs at a temperature of about 600° C. or less and is an equilibrium reaction accompanied by a large amount of heat generation. When the temperature rising of the reaction gas, methane decomposition (steam reforming reaction) in the opposite direction to the methanation reaction becomes dominant, resulting in a decrease in conversion ratio and yield. As a result, the methane gas produced by this reaction contains high concentration of highly explosive hydrogen unreacted, making it difficult to obtain safe and easy-to-use methane.

Today, the main industrial use of this technology to convert into methane using hydrogen is limited to remove carbon dioxide, which is a reaction inhibitor in ammonia synthesis process, and slightly contained in the gas as described in Non-Patent Document 2.

In this case, since the reaction heat of methanation of a small amount of carbon dioxide is diluted with a large amount of surrounding gas, the influence of heat generation is negligibly small and does not become an obstacle. However, in the reaction of hydrogen with a high concentration of carbon dioxide having a concentration close to 100% in the absence of such a diluted gas, the influence of heat generation is large, and the heat removal of the catalyst surface, which is the reaction field, becomes insufficient. As described above, in addition to the decrease in the conversion ratio to methane due to the increase in temperature, the catalyst itself deteriorates due to the heat. Furthermore, since the removal of the heat generated is not easy, it is one of the reasons why the process of producing methane from high-concentration carbon dioxide and hydrogen has not been put to practical use until now.

However, in recent years, as the necessity for global warming countermeasures has increased, according to Non-Patent Document 6, catalysts with high activity at low temperatures have been developed, and according to Patent Document 1 and Non-Patent Documents 4-5, the development and demonstration tests of the reactors that are devised to remove the reaction heat generated or to control the amount of reaction are proceeded.

Further, in Patent Document 1, carbon dioxide obtained by recovering carbon dioxide in flue gas by using an amine-based absorption method is used as the carbon dioxide that is the raw material for this methanation method. That is, investigation and development of a process for converting green hydrogen into methane using carbon dioxide in flue gas are underway.

PRIOR ART LITERATURE

Patent Documents

[Patent Document 1]:
    In Japanese Patent Application No. 2016-524796 (PCT/EP2014/064625) and Japanese Patent Application No. 2020-63206, the following method is described. Carbon dioxide which obtained from flue gas by absorption methods such as the above-mentioned amine-based absorption method and hydrogen are used to produce methane.

In this method, the heat obtained by heat removing from the methanation reactor is used for preheating the boiler combustion air.

[Patent Document 2]:
    Japanese Patent application No. 2020-71387 proposed moving beds and multi-stage fluidized beds equipped with a swinging mechanism that prevents the occurrence of the drift and enables uniform contact between gas and solid by giving horizontal swinging motion to fine powder, which is particularly difficult to fluidize.

Non-Patent Literature

[Non-Patent Document 1]
    Paul Sabatier proposed that carbon dioxide and hydrogen react to produce methane in the presence of a Ni catalyst in "Catalysis in Organic Chemistry" of 1913.

[Non-Patent Document 2]
    According to "Tsunekichi Kuriyama, Chemistry and Education 66 (11), P529 (2018)", the methanation reaction is used to remove traces of carbon dioxide in the industrial production of ammonia is described.

[Non-Patent Document 3]
    According to https://www.nedo.go.jp/news/press/AA5_101330.html, on Jul. 13, 2020, in collaboration with Kawasaki Heavy Industries, Ltd. and the Research Institute of Innovative Technology for the Earth, NEDO has introduced "carbon dioxide separation and recovery technology using a solid absorption method" using particles impregnated with amine. They are developing a methane production process and are working to reduce the cost of carbon dioxide separation and recovery technology.

[Non-Patent Document 4]

In "Review on methanation—From fundamentals to current projects" Pages 276-296. Fuel 2016, 166 by Stefan Ronsch and others, the reviews of methanation process technologies and their issues are summarized respectively.

[Non-Patent Document 5]

According to https://www.nedo.go.jp/news/press/ AA5_101217.html, in a news release dated Oct. 16, 2019, the New Energy and Industrial Technology Development Organization (NEDO), INPEX CORPORATION, and Hitachi Zosen Corporation jointly announced the development of "Methane Synthesis Test Facility utilizing Carbon Dioxide" has been completed, and commissioning has begun in preparation for full-scale operation.

[Non-Patent Document, 6]

In "University of Toyama Hydrogen Isotope Science Research Center Research Report", 36, 39-44, (2016), Abe et al reported, when TiO2 particles supporting nanometer-sized Ru metal catalysts was active at low temperatures of 150 to 200° C.

[Non-Patent Document 7]

In "Journal of Ceramic Society of Japan", 71, P61, (1963)", Kenya Hamano reported that the dehydration reaction of magnesium hydroxide is about 2% until about 290° C., and when it exceeds 330° C., dehydration begins rapidly, and it will be completed by 430° C.

[Non-Patent Document 8]

In "Journal of the Chemical Society of Japan, p. 57-64, (1979)", Yutaka Sawada, et al. reported the measurement results of the thermal decomposition process of basic magnesium carbonate.

[Non-Patent Document 9]

In "Chemical Engineering 31 (6), P538 (1967)", Shiro Maeda, Norio Yamakawa reported that the fluidized bed has a large heat transfer coefficient.

[Non-Patent Document 10]

In "Examples and Issues of Technologies for Chemically Storing Exhaust Heat": Society of Automotive Engineers of Japan No. 14-14 Symposium, Feb. 13, 2015 by Takayuki Kobayashi, FIG. 5 in http://www.energy.gr.jp/wp-content/uploads/ 2018/02/ChHeatStorage.pdf shows various chemical heat storage agents and their operating temperatures. Among them, magnesium hydroxide and magnesium carbonate are indicated as chemical heat storage agents that can be operated in the range of 300 to 500° C.

Problems to be Solved by the Invention

The absorption temperature of the carbon dioxide in the absorption method using an amine-based absorbents is depends on the types of amines, it is said to be approximately 20° C. to 60° C., which is lower than the normal flue gas temperature (approximately 140° C.). Therefore, in order to absorb the carbon dioxide in the flue gas, the flue gas temperature is necessary to lower once.

Lowering the flue gas temperature reduces the "Effective Height of Stack" specified in the Air Pollution Control Law.

It is considered necessary to raise the temperature to around 140° C. again, or to strengthen the exhaust blower and increase the wind speed of the exhaust gas. In addition, it is known that the amine-based absorbent reacts with a small amount of SOx in the flue gas after the desulfurization process and gradually deteriorates, so periodic refining and replenishment of the absorbent are required.

Therefore, a new method capable of absorbing and fixing carbon dioxide without lowering the flue gas temperature and without deterioration of the absorbent is required.

On the other hand, the methanation reaction for synthesizing methane from carbon dioxide and hydrogen is represented by Reaction Formula 1. As already mentioned, this reaction is an equilibrium reaction and an exothermic reaction.

Here, the value of the Gibbs free energy change $\Delta G$ of the methanation reaction is given by Equation 1 using the value of the Gibbs free energy G of each component involved in this reaction. When the value of Equation 1 is negative, the reaction proceeds, and when it is positive, the reaction proceeds in the opposite direction that is a reverse reaction. Therefore, $\Delta G$ from 0 to 1000° C. was calculated for Reaction Formula 1, and the results are shown in FIG. 1. In general, the values of $\Delta G$ and enthalpy change $\Delta H$ at each temperature for many compounds can be quoted from various thermodynamic databases such as chemical handbooks. Here, these values were calculated by using ASPEN PLUS as the process simulator having these data bases. From FIG. 1, the $\Delta G$ value of the methanation reaction is zero around 580° C., and is negative below this temperature, so the methanation reaction proceeds, but above 580° C., the $\Delta G$ value turns positive, so the reverse reaction (the steam reforming reaction of methane) becomes dominant.

Further, when the enthalpy of each component is calculated, the reaction in which methane is produced in reaction formula 1 is an exothermic reaction, but the steam reforming reaction, which is the reverse reaction, is an endothermic reaction.

In general, the reaction rate of an endothermic reaction is governed by the amount of heat given, so it is easy to control the reaction rate. But, in the case of the exothermic reaction and Arrhenius type reaction, when the heat removal capacity of the reaction heat are shortage, the reaction temperature is raised and the reaction rate also increases as the reaction temperature rising, as the result the reaction may lead to runaway.

However, in the case of this methanation reaction, when the temperature rises, the reverse reaction becomes dominant, so although it does not lead to runaway reaction, the reaction yield decreases. Therefore, it is important to have sufficient heat removal capacity to suppress the reaction temperature rising.

$$CO_2+4H_2 \leftrightarrows CH_4+2H_2O \qquad \text{[Reaction Formula 1]}$$

$$\Delta G=(G_{CH_4}+2G_{H_2O})-(G_{CO_2}+4G_{H_2}) \qquad \text{[Equation 1]}$$

In addition, since this reaction occurs on the surface of the catalyst, the temperature of the catalyst tends to rise due to heat generated by the reaction. When heat is not quickly removed from the catalyst, the temperature of the catalyst rises, as already described, and as a result, not only does the conversion ratio decrease, but also the life of the catalyst also shortens.

Therefore, the problem to be solved in this methanation reaction is the rapid removal of reaction heat from the reaction field containing the catalyst.

Next, the methanation reaction proceeds below 580° C. The dehydration reaction of magnesium hydroxide in Reaction Formula 2 is an endothermic reaction, since the value of ΔG is negative above about 270° C. in FIG. 1, it means that this dehydration reaction proceeds. In fact, it is almost consistent with the report in Non-Patent Document 7 that "the dehydration reaction of magnesium hydroxide occurs above 300° C."

Next, it can be seen from FIG. 1 that the decarboxylation reaction of magnesium carbonate in Reaction Formula 3 also proceeds because the value of ΔG is negative above 410° C. In fact, according to Non-Patent Document 8, the decarboxylation reaction depends on the carbon dioxide concentration in the atmosphere, but it is consistent with the report that all decarboxylation occurs above 400° C. when the carbon dioxide partial pressure is less than 5 mol %.

From both of these dehydration and decarbonation reactions, magnesium oxide is generated, but the calculation line of the dehydration reaction of magnesium hydroxide is in positive range below 270° C. in FIG. 1. This means that the reverse reaction (hydration) proceeds below this temperature. That is, as shown in Reaction Formula 4, magnesium oxide returns to magnesium hydroxide by reacting with water. Furthermore, in the carbonation reaction of magnesium hydroxide in Reaction Formula 5, the calculation line in FIG. 1 is a negative region over a wide temperature range, it means that the carbonation proceeds even below 600° C. Therefore, the carbonation is expected to proceed even at flue gas temperatures of 140° C.

$$Mg(OH)_2 \rightarrow MgO + H_2O \qquad \text{[Reaction Formula 2]}$$

$$MgCO_3 \rightarrow MgO + CO_2 \qquad \text{[Reaction Formula 3]}$$

$$MgO + H_2O \rightarrow Mg(OH)_2 \qquad \text{[Reaction Formula 4]}$$

$$Mg(OH)_2 + CO_2 \rightarrow MgCO_3 + H_2O \qquad \text{[Reaction Formula 5]}$$

Now, the equilibrium constant K of the reaction at an arbitrary temperature T can be obtained from ΔG by Equation 2, where R is the gas constant. Furthermore, from Reaction Formula 1, the relationship between this equilibrium constant K and the concentration of each component is given by Equation 3. Namely, from the value of ΔG at an arbitrary temperature T, the value of K can be obtained from Equation 2, and then from the value of K, the equilibrium composition of each component at an arbitrary temperature can be calculated from Equation 3. The equilibrium composition according to Equation 3 is determined by a trial and error method. The methanation reaction at each temperature will proceed to approach this equilibrium composition.

FIG. 2 is the graph showing the changes of the equilibrium conversion ratio of carbon dioxide according with temperature change, which was determined in this way. In this figure, the solid line indicates the case where the reaction gas is not diluted with steam, and the dashed line indicates the change in the equilibrium conversion ratio when 1 mol of steam is added to the reaction gas. As will be described later, this corresponds to the case where magnesium hydroxide absorbs reaction heat and dehydrates to generate 1 mol of water vapor.

At a temperature of around 580° C., the conversion ratio of carbon dioxide to methane is 50%. And at around 350° C., the equilibrium conversion ratio is about 87% shown by the dashed line, and then unreacted carbon dioxide is reduced to about 13%.

$$K = \exp\left(-\frac{\Delta G}{RT}\right) \qquad \text{[Equation 2]}$$

$$K = \frac{[CH_4][H_2O]^2}{[CO_2][H_2]^4} \qquad \text{[Equation 3]}$$

Furthermore, from FIG. 2, it can be seen that it is effective to proceed the reaction at a lower temperature in order to obtain a high conversion ratio to methane. That is, in this reaction, the lower the reaction temperature is, the higher the conversion ratio of the reaction is. Therefore, in order to increase the conversion ratio at the outlet of the reactor, it is effective to lower the reaction temperature as the reaction progresses.

However, as already mentioned, this reaction generates heat when it reacts, so if the heat removal capacity is not sufficient, this reaction heat raises the temperature and conversely lower the conversion ratio. On the other hand, in terms of reaction kinetics, the lower the reaction temperature is, the lower the reaction rate is. Therefore, the higher the reaction temperature, the better. This is the dilemma of this methanation reaction and a problem to be addressed.

Therefore, in the initial stage of the reaction, the reaction temperature is raised to proceed the reaction, but after that, the reaction is carried out while gradually lowering the reaction temperature, and at the outlet of the reaction apparatus where the temperature becomes low, the reaction rate should be increased. The reaction apparatus which is capable of increasing the conversion ratio to methane without lowering the reaction rate even in a low temperature region by increasing the catalyst concentration or using a catalyst having higher activity is required.

Here, an overview of the past main research and development progress is as follows.

The methanation reaction in Patent Document 1 and Non-Patent Documents 4-5 is carried out in the presence of a Ni-based catalyst at a temperature range of 300 to 400° C.

Further, processes has been proposed in which the heat obtained from this heat removal is used inside or outside of the process.

Regarding the catalyst, the catalyst is molded into pellets or honeycombs, filling these in a reaction tube, passing a reaction gas through this reaction tube, and an indirect cooling method, in which the heat generated in the reaction tube is removed by cooling from the outside of this reaction tube, is used.

In a reactor for reaction at 300 to 400° C., the equilibrium conversion ratios when the outlet temperature of the reactor is 350° C. and 300° C. are about 87% and 92%, respectively, according to FIG. 2.

In order to bring the actual conversion ratio close to the equilibrium conversion ratio, it is necessary to secure a sufficient reaction time. Assuming that the conversion ratio in the methanation reactor proceeds to 90%, the composition of the gases generated from the raw material gas (1 kmol carbon dioxide and 4 kmol hydrogen) are 0.90 kmol of methane and 1.80 kmol of water vapor, And, the composition of the unreacted gas are 0.10 kmol of carbon dioxide and 0.40 kmol of hydrogen. When converted to a concentration, the concentration of unreacted hydrogen is 12.5 mol %, and it is dangerous and undesirable to use methane containing such a high concentration of highly explosive hydrogen as a fuel for general use.

In recent years, according to Non-Patent Document 6, a Ru-supported catalyst having higher activity even at 150 to 200° C. has been developed in order to further increase the conversion ratio. Therefore, the reaction is first carried out at 300 to 400° C., then the generated gas is cooled to 150° C., and if the reaction is further proceeded in the presence of this catalyst, the conversion ratio would be able to approach to 0.98 which is the equilibrium conversion ratio.

When the conversion ratio is 0.98, the concentration of unreacted hydrogen will be reduced to 2.6 mol %. That is, the danger of the generated methane can be greatly reduced. Summarizing the above, increasing the conversion ratio to methane in the methanation reaction reduces the concentration of unreacted hydrogen in the product gas, which is important not only from the reaction yield but also from the viewpoint of safety. For this reason, after the reaction at 300-400° C., it is necessary to add a reactor for further reaction at 150-300° C. to increase the equilibrium conversion ratio to nearly 98%.

Before proceeding to the specific structure of the device, the elements of the device should be organized. For this reason, it is assumed that the methanation reaction is performed by connecting reactors in a plurality of different temperature ranges in which the temperature is lowered stepwise from 500° C. to 200° C. in 100° C. each.

That is, in the first stage, a conventional catalyst is used to proceed the reaction in the temperature range of 400-500° C., and then before entering the second stage, the reaction gas is cooled down to react in the range of 300-400° C.

Furthermore, in the third stage, this is similarly cooled to a range of 300 to 200° C. At this temperature, the reaction rate drops significantly, so Ru catalyst which has high activity described in Non-Patent Document 6 in this temperature range is assumed to use for this reaction.

In this way, by lowering the reaction temperature as the reaction proceeds and using a catalyst with higher activity in the lower temperature region, the conversion ratio can be increased without significantly decreasing the methanation reaction rate, then, the remaining unreacted hydrogen concentration can be lowered, and produced methane which can be used safely.

However, in this process, it is necessary to connect multiple reactors and install a cooler to lower the gas temperature between them, which means the process would become complicate.

A compact reactor which has high heat removal performance and can lower the reaction temperatures as the reaction progresses is desired. If such a reactor is realized, it should be possible to increase the final conversion ratio of the methanation reaction and reduce the concentration of unreacted hydrogen with this compact reactor.

[Means to Solve Problems]

In the case of the three-stage reactor as described above, a cooler is required between each reactor to lower the reaction gas temperature, resulting in a complicated process. So, a compact process that does not need coolers is required.

According to Non-Patent Document 9, the fluidized bed is a reactor having an excellent heat transfer performance. In the present invention, in order to solve the problem of heat removal, a fluidized bed having an excellent heat transfer performance is used, and the reaction gas supplied from the bottom of the reactor is used as the fluidizing gas.

FIG. 3 shows the concept of a one-stage fluidized bed methanation reactor that uses inorganic powder as a fluidizing medium and reaction gas as a fluidizing gas. The configuration of the apparatus is the same as that of a normal fluidized bed apparatus. That is, there is a dispersion plate 4 at the bottom of the fluidized bed reactor 1, the powder bed 2 of fluidizing medium is above it. The powder is fluidized by the reaction gas 3 passing through the dispersion plate 4.

The catalyst is placed in this fluidizing powder as particles or honeycomb shapes, which is not shown in this figure.

The heat transfer tube 5 for heat removing is also immersed in this fluidized bed and the generated heat in this fluidized bed is absorbed and removed by cooling the fluidizing powder by passing through cooling water or thermal media oil into the tube 5. The mixing characteristic of the fluidized bed is a complete mixing, and its high heat transfer performance makes almost uniform temperature distribution in the bed. Therefore, the temperature in this reactor cannot lower as the reaction proceeding. Therefore, in the case of this one-stage fluidized bed, when the reaction temperature is 300 to 400° C., as described above, the concentration of residual hydrogen in the resulting methane exceeds 10%.

Next, by lowering the reaction temperature of this fluidized bed to 200-300° C., it is possible to increase the conversion ratio and reduce the residual hydrogen concentration, but it means that the lower the temperature is, the lower the reaction rate is. Therefore, in order to increase the reaction rate, it is necessary to take counter measures such as using a highly active catalyst, increasing the amount of catalyst, or increasing the residence time of the reaction gas in this reactor, that is, increasing the size of the reactor.

From the above studies, as a preferable reactor, in order to improve the conversion ratio to methane at the outlet of the reactor, as already mentioned, a plurality of fluidized bed reactors having different inside temperatures are connected in series. As an example, the conversion ratio can be further improved by supplying the gas to a reactor at 300-400° C. and then passing the outlet gas from this reactor to the next reactor at 150-300° C.

Therefore, in the present invention, a multi-stage fluidized bed is applied in which a plurality of such fluidized-bed reactors can be integrated into one reactor. Its concept is shown below.

Cooling the powder which is fluidizing medium using in the multi-stage fluidized bed to the temperature or lower than the temperature of the fluidizing medium in the uppermost stage of the multi-stage fluidized bed by using a powder cooler provided outside of the multi-stage fluidized bed, then, the cooled powder is continuously fed into the uppermost stage of this multi-stage fluidized bed reactor. And, while the powder is flowing down inside of the multi-stage fluidized bed, its temperature is rising by absorbing the heat inside of the reactor. The powder which became higher temperature by absorbing the heat is continuously extracted. Then, this powder is cooled by the external cooler describe above and is circulated into the uppermost stage of the multi-stage fluidized bed. Whereby the temperature distribution is formed, in which the temperature of the lowermost stage is the highest, the temperature of uppermost stage is the lowest and the temperature of each stage between the uppermost and lowermost stages are gradually lowered from the bottom to top.

The concept and configuration of this sort of reactor in which the fluidizing medium is externally cooled and circulated to form the temperature distribution described above is similar to a multi-stage distillation column. In the distillation column, the liquid is heated by a reboiler at the bottom of the column to evaporate, and the vapor coming out from the top of the column is cooled and condensed by an external condenser, and part of this condensate is refluxed into the column. By refluxing the cooled condensate to the top of the column, a stepwise temperature distribution in which the top temperature of the column is low and the bottom temperature of the column is high is formed. Refluxing the cooled and condensed liquid is similar to charging the powder cooled by the external cooler of the multi-stage fluidized bed of the present invention to the uppermost stage to cool the inside of the reactor.

FIG. 4 is a schematic diagram of a two-stage fluidized bed for more specifically explaining this concept. In order to lower the temperature of the upper stage of the reactor, the powder cooled by the external cooler 11 and whose temperature is lower than that of the upper stage of the reactor is continuously fed to the upper stage of this fluidized bed reactor 1 through the powder transporting pipe 13. That is, instead of lowering the temperature of the upper stage of this two-stage fluidized bed by means of cooling heat transfer tubes, the internal temperature is lowered by feeding the cooled powder to lower-temperature. As a result, the temperature of the upper stage of the fluidized bed 1 is lower than that of the lower stage of the fluidized bed 7. The powder fed into the upper stage absorbs the reaction heat of the internal gas and the sensible heat of the temperature drop of the gas, rises in temperature, and then enters the fluidized bed 7 in the lower stage.

In the lower-stage fluidized bed, the lower-temperature powder flowing down from the upper stage absorbs the reaction heat and sensible heat of the gas in this region and then raises the temperature of itself, thereby suppressing the temperature rising of the fluidized bed 7.

As the result, the upper stage temperature of the fluidized bed becomes lower than the lower stage temperature of the fluidized bed, on the other hand, while the reactant gas reacts in the lower stage of the fluidized bed where the temperature is higher, and then flowing up into the upper stage where the temperature is lower than that of the lower stage. By lowering gas temperature, the equilibrium conversion ratio is further increased, and by using a catalyst with higher activity at low temperature, the reaction is further proceeded. Eventually, increasing the conversion ratio to methane and lowering the residual hydrogen concentration becomes possible.

Since the powder is continuously fed from the upper stage, it is necessary to continuously extract the amount of the powder heated to higher temperature corresponding to the moles fed from the discharging section 9 of the fluidized bed 7 in the bottom of lower stage. The extracted high-temperature powder is fed into the upper part of the moving bed 12 in the external heat exchanger 11, cooled inside, extracted from the bottom, and fed again through the powder transport pipe 13 for methanation. That is, it is fed into the upper stage of the fluidized bed 1 of the reactor. The configuration of the reaction gas 3, the dispersion plate 4, and the heat removal tube 5 is the same as in FIG. 3.

The above is the meaning and effect of using a multi-stage fluidized bed and circulating the fluidizing medium between it and the external powder cooler. The above is a simplified two-stage fluidized bed for explaining the concept of the present invention. In the case of the applying this method to a methanation reaction, the temperature varies greatly from about 600° C. to about 150° C., so a multi-stage fluidized bed having three or more stages is preferable.

Next, a more detailed description of the multi-stage fluidized bed having such a temperature distribution will be given. Here, the temperature of the uppermost stage of the multi-stage fluidized bed is assumed in the range of 140-200° C., the temperature of the lowest stage is assumed in the range of 300-500° C., and the temperature in each intermediate stage is assumed to decrease from the lowest to the highest in order. In each stage, catalyst particles or catalyst moldings are arranged, and carbon dioxide and hydrogen, which are reaction raw materials, are supplied as fluidizing gases from the bottom of this multi-stage fluidized bed. The powder in the fluidized bed is fluidized by this gas flow and then the gas is brought into contact with the catalyst in the fluidized bed to synthesize methane. Since in the temperature range of 140-200° C. at the uppermost stage of the reactor outlet, the equilibrium conversion ratio to methane increases as the reaction temperature decreases, the lower concentration of unreacted residual hydrogen and the higher methane concentration comparing to the methane obtained from a conventional single methanation reactor with a reaction temperature of 300-500° C. are enabled to obtain.

In this multi-stage fluidized bed, the falling powder and the rising gas are brought into direct counter-current contact and heat is exchanged, similar to a tray-type distillation column. As a result, without using a powder heater or a gas cooling device between multiple stages of fluidized beds with different temperatures, a multi-stage fluidized bed, in which the temperature of the uppermost stage is the lowest and the temperature of the lowest stage is the highest, is realized. Such configuration greatly simplifies the device and is one of the great features of the present invention.

In addition, hot spots may generally occur in a packed bed reactor filled with a catalyst that causes an exothermic reaction. Since the fluidized bed has high heat transfer performance, the temperature distribution is uniform, it is expected that the longer life of the catalyst will be extended as compared with the conventional packed bed type reactor.

Next, the powder used as the fluidizing medium for this multi-stage fluidized bed is desirably safe inorganic compounds which are inexpensive, stable, and have no toxicity or environmental load. Namely, as sand, silica, alumina, magnesia, calcia are such candidate.

Here, the heat load of each stage of this multi-stage fluidized bed will be described by taking a multi-stage fluidized bed having a three-stage configuration as an example.

As an explanation of the concept of the apparatus of the present invention, a three-stage multistage reactor with every temperature changes of 100° C. from 200° C. to 500° C. is assumed. The reaction gas injected at the bottom stage of the reactor at 500° C. and flows into the next upper stage at 400° C.

The left side bar of the three vertical bars shown in FIG. 2 show the equilibrium conversion ratio in the temperature range of 400 to 500° C. in this multi-stage fluidized bed and the relative reaction amount to reach this conversion ratio. Next, this gas rises and enters the upper stage of the fluidized bed in which the temperature range is 300 to 400° C., and indicates the increment of the conversion ratio when the reaction proceeds further and the relative increased reaction amount. Furthermore, it also shows an increase in the reaction amount in the range of 200 to 300° C. The reaction amount in the range of 400 to 500° C. is the reaction from zero conversion ratio, i.e., it means that the amount of heat generated is relatively large on the bottom side of this reactor. From here, the numerical values of the equilibrium conversion ratios in FIG. 2 are read, and the generated heat in each stage is roughly estimated.

The equilibrium conversion at 450° C. is 80% from the dashed line in FIG. 2. Assuming that the actual reaction ratio reached is 80% of this equilibrium conversion ratio, the amount of reaction in this stage would be 64% of the total reaction. This indicates that 64% of the exothermic value of the methanation reaction occurs in this temperature region.

On the contrary, the equilibrium conversion ratio at 350° C. region in the next stage is 92% from FIG. 2. Similarly, when the actual conversion ratio is 80%, the conversion ratio to methane is 74%. It means that from 64% in 450° C. region to 74% at 350° C. region, the reaction proceeds another 10%. That is, the required amount of heat removal in the lowest stage is larger than that in the second stage because its reaction amount is from zero conversion and is large about 6.4 times comparing to that of the second stage. Therefore, it is necessary to remove a large amount of heat in the lowermost fluidized bed, and it is necessary to strengthen the heat removal capacity by increasing of the heat transfer area, such as installing a large number of heat transfer tubes.

To solve this problem, the present invention uses the inorganic powder already described as the fluidizing medium, and further mixes the powder of substances that decompose by absorbing heat in the range of 300 to 600° C. into the powder. Thereby, it was devised that part or all of the exothermic heat of the methanation reaction generated in the multi-stage fluidized bed reactor in the temperature range of above 300° C. is absorbed by the decomposition reaction of these compounds.

As a substance that absorbs heat and decomposes in the range of 300 to 600° C. and can be regenerated after decomposition, magnesium hydroxide powder is a chemical heat storage agent shown in Non-Patent Document 10, that is, is dehydrated and absorbs heat according to Reaction Formula 2 above 300° C., and magnesium carbonate powder is decarbonated above 400° C. according to Reaction Formula 3. By using these substances, a part or all of the reaction heat of the methanation that occurs in the temperature range above 300° C. in this multi-stage fluidized bed reactor can be absorbed by these endothermic reactions of these chemical heat storage agents. Therefore, in the present invention, the heat removal capacity in this temperature range is strengthened by using these substances.

That is, the lowermost stage which is the inlet of the reaction gas of this multi-stage fluidized bed generates large reaction heat, and it is necessary to strengthen its heat removal capacity. By using endothermic agents that proceed endothermic reactions in this temperature range, and mixed with the fluidizing medium flowing down from the uppermost stage to the lowermost stage, the heat removal load in this temperature range can be greatly reduced.

The endothermic reactions of these chemical heat storage agents, that is, the dehydration reaction of magnesium hydroxide produces magnesium oxide, and the decarbonation reaction of magnesium carbonate also produces magnesium oxide.

As shown in reaction formula 4, this magnesium oxide can be regenerated as magnesium hydroxide by a hydration reaction with water. Furthermore, as shown in reaction formula 5, this magnesium hydroxide can be regenerated as magnesium carbonate by reacting with carbon dioxide. That is, it is possible to regenerate this magnesium oxide as magnesium hydroxide and then magnesium carbonate and recycle them repeatedly.

Since both of these two regeneration treatment reactions are exothermic reactions, it means that the reaction heat absorbed in the methanation reactor is recovered and utilized during these regeneration treatments.

Here, when this carbonation reaction is carried out by absorbing carbon dioxide in the flue gas of the factory, it means that this carbon dioxide is fixed as magnesium carbonate. Furthermore, when this magnesium carbonate is used as a supplying source of carbon dioxide, which is one of the raw material gas for this methanation, it means that carbon dioxide in this magnesium carbonate is converted into methane. That is, methane can be produced from the carbon dioxide in the flue gas, this is one of the CCUS technology.

Also, at this time, when using "green hydrogen" as the hydrogen to be used for synthesizing methane, it means that fuel, which is easy for us to use, is synthesized from renewable energy and greenhouse gas, or that green hydrogen is converted into more usable methane with global warming gas.

Another feature is that the apparatus used for this methanation reaction is a multi-stage fluidized bed, so it is possible to select and use the different optimum catalyst for each temperature range of the each stage.

In addition to catalysts that are usually used at 300-500° C., catalysts which have high activity at low temperatures have been developed. So, in the low-temperature region of the multi-stage fluidized bed, the catalyst for low temperature having high activity even in the low temperature range of 150 to 200° C. can be used. In the high-temperature region of this fluidized bed, conventional methanation reaction catalysts such as Ni catalysts can be used, and in the intermediate temperature region between these, it is possible to select any one of these or to use a mixture of these catalysts.

That is, in a reactor using the multi-stage fluidized bed in which the temperature decreases as the reaction proceeding, by selecting and using the different optimum catalyst for each temperature range, high-concentration methane can be synthesized without slowing down the reaction rate even in the exit side of the reactor where reaction temperature decreases and the reaction rate decreases.

In this type of reactors, in order to prevent moving down of these catalysts with the fluidizing medium to the lower stages of the multi-stage fluidized bed, the catalyst particles should be made larger than the hole diameter of the down corner or the catalysts should be molded into a honeycomb shape to hold in each stage.

Next, since the chemical heat storage agent mixed in the fluidizing medium is powder, it is preferable to use fine powder having a high specific surface area in order to increase the reaction rate. In this case, it is generally considered difficult to fluidize the fine powder, so it is necessary to provide a means for fluidizing the fine powder.

[The Effect of the Present Invention]

The above was a conceptual description of the present invention, in the following, the feasibility of the idea of removing the reaction heat, which is the concept of the present invention, by absorbing the heat by the endothermic reaction of the chemical heat storage agent, will be verified by heat calculation.

Table 1 shows the exothermic value and endothermic value of each reaction under standard conditions. In addition, the reaction starting temperature of each reaction is shown in the rightmost column.

First, the bottom row of this table shows the combustion heat when 4 kmol of hydrogen is burned and the value is 968 MJ/kmol. The second row from the lowermost row shows the combustion heat of methane, which is 803 MJ/kmol. The difference between the two is 165 MJ/kmol, which corresponds to 17% of the heat of the combustion of hydrogen.

Next, the third row from the lowermost row shows the generating heat value when 4 kmol of hydrogen reacts with 1 kmol of carbon dioxide to make 1 kmol of methane, which is 165 MJ/kmol and is equal to the difference between the combustion heat of hydrogen and that of methane. In other words, this difference means that a part of energy possessing by 4 kmol of hydrogen is released to the outside as reaction heat when it is converted into methane.

This calculation shows that direct combustion of hydrogen is more advantageous than using methane converted from hydrogen, from the quantitative point of view of energy. However, hydrogen needs to be stored under high pressure, and is a substance with a high risk of hydrogen explosion if leaked, and must be equipped with strict safety equipment for safe use.

On the other hand, since methane is a fuel used in household gas stoves and the like, it is preferable to convert it into methane and use it safely because it can be used safely using the existing infrastructure. However, by converting into methane, the amount of energy is reduced by 17%, so a method is desired to recover and effectively utilize this 17% heat as much as possible.

In the present invention, by utilizing the dehydration reaction of magnesium hydroxide and the decarbonation reaction of magnesium carbonate, which endotherm above 300° C., the 17% of this loss of heat can be absorbed and stored in the magnesium oxide produced. If this stored heat is used effectively in other processes, this 17% energy will not be a loss.

First, the dehydration reaction of magnesium hydroxide proceeds above 300° C., and its endothermic amount is 81 MJ/kmol, next, the endothermic amount of the decarbonation reaction of magnesium carbonate is 118 MJ/kmol, and the sum of them is 199 MJ/kmol. That is, since it is larger than the exothermic heat of the methanation reaction, which is 165 MJ/kmol, all the reaction heat of the methanation reaction can be absorbed and stored by adjusting these two reaction amounts.

Although the above study was conducted using the enthalpy under the standard state, the actual calculation should be performed using the enthalpy value at each reaction temperature. The reaction and heat calculation at each reaction temperature are described below.

TABLE 1

| | | Reaction Heat at 298 K [MJ/kmol] | | Temp. |
|---|---|---|---|---|
| | Reaction | Exo | Endo | Range |
| Hydration | $MgO + H_2O \rightarrow$ $Mg(OH)_2$ | 81.2 | | below 250° C. |
| Carboxylation | $Mg(OH)_2 + CO_2 \rightarrow$ $MgCO_3 + H_2O$ | 37.1 | | below 400° C. |
| Dehydration | $Mg(OH)_2 \rightarrow$ $MgO + H_2O$ | | 81.2 | above 330° C. |
| Decarboxylation | $MgCO_3 \rightarrow$ $MgO + CO_2$ | | 118.3 | above 400° C. |
| Methanation | $CO_2 + 4H_2 \rightarrow$ $CH_4 + 2H_2O$ | 165 | | 150~580° C. |
| Combustion of Methane | $CH_4 + 2O_2 \rightarrow$ $CO_2 + 2H_2O$ | 803 | | |
| Combustion of H2 | $4H_2 + 2O_2 \rightarrow 4H_2O$ | 968 | | |

FIG. 11 shows the reaction amount and reaction heat of the methanation reaction in two temperature ranges of 300 to 400° C. and 400 to 500° C., and the corresponding endothermic reaction and amounts of the endothermic heat of them. In the following, in these two temperature ranges, it is shown that all of the exothermic value due to the methanation reaction can be offset by these endothermic reactions.

First, the heat calculation is performed with the intermediate temperature of 450° C. for calculating the reaction heat in the temperature range of 400 to 500° C. The reaction heat of the methanation at 450° C. is 183 MJ/kmol, which is higher than the value of the standard state at 25° C. Next, since the equilibrium conversion ratio at 450° C. is 0.72 from FIG. 2, assuming the reaction reaches this equilibrium conversion ratio, the exothermic heat is 132 MJ/kmol. On the other hand, the decarbonation heat of 1 kmol magnesium carbonate at 450° C. is 114 MJ/kmol. Therefore, 18 MJ/kmol of methanation reaction heat of 1 kmol is excessive and cannot be absorbed.

Next, when the temperature for heat calculation in the temperature range of 300 to 400° C. is carried out, the intermediate value of 350° C. is taken as temperature to be calculated. The equilibrium conversion ratio of 350° C. is 0.90 from FIG. 2, so assuming that the conversion ratio of the reaction proceeds from 0.72 to 0.90, the increment of the conversion ratio is 0.18, and the reaction amount of carbon dioxide at this time is 0.18 kmol. Also, since the reaction heat of the methanation at 350° C. is 180 MJ/kmol, the reaction heat of this temperature range is 32 MJ/kmol. Summation of this value with the surplus heat of 18 MJ/kmol in the 400-500° C. range, the heat to be removed is 50 MJ/kmol. On the other hand, since the heat of dehydration reaction of 1 kmol magnesium hydroxide at 350° C. is 76 MJ/kmol, this 50 MJ/kmol heat can be absorbed by the dehydration reaction of 0.66 kmol magnesium hydroxide. Therefore, all of the methanation reaction heat above 300° C. can be absorbed and be offset by decarbonation of 1 kmol magnesium carbonate and dehydration of 0.66 kmol magnesium hydroxide. That is, temperature rising in the reactor can be suppressed without using heat transfer tubes for heat removal.

FIG. 11 assumes that 18 MJ/kmol of heat from 400-500C is brought to the temperature region of 300-400°. In addition as another way, the decarbonation reaction of 1.16 kmol of magnesium carbonate absorbs all heat of 132 MJ, next, 32 MJ of heat can absorbs by the dehydration reaction of 0.42 kmol of magnesium hydroxide, and then all of the reaction heat of 1 kmol methanation can be absorbed by these endothermic reactions. In this case, all of the reaction heat is absorbed without bringing the heat in the 400-500° C. region to the 300-400° C. region.

The above described means that the heat removal from the high temperature section of 300 to 500° C., where the amount of heat generated by the reaction is large, can be absorbed without using the heat removal method using heat transfer tubes and by using appropriate amount of these chemical heat storage agents in the methanation reactor. Furthermore, this indicates that generated heat by exothermic reaction can be stored in magnesium oxide.

These two endothermic reactions generate 1.66 kmol of magnesium oxide in the former case and 1.58 kmol in the latter case. It can be regenerated as magnesium hydroxide by hydration with water, then by reacting this magnesium hydroxide with carbon dioxide, it can be regenerated and used as magnesium carbonate. Moreover, since these regeneration reactions are both exothermic reactions, it is possible to recover and utilize the heat absorbed in the methanation reactor during this regeneration.

In other words, by converting hydrogen into methane and using it, 17% of the energy possessed in hydrogen is reduced, and it will drop to 83%. However, by absorbing this loss of heat in the heat storage agents and using it during regeneration, a part or all of this 17% energy loss can be used effectively instead of being lost.

As described above, the features of the methanation reactor of the present invention are as follows.

1. A fluidized bed with high heat transfer performance is used for the reactor instead of the conventional packed bed, a reactive gas is used as the fluidizing gas, and inorganic powder is used as the fluidizing medium.

2. The powder as fluidizing medium cooled by the external cooler is fed into the top of the multi-stage fluidized bed reactor and allowed to flow down and to absorb reaction heat inside of the reactor, then the powder raised to a high temperature is extracted from the bottom. By circulating the fluidizing medium between the external cooler and the multi-stage fluidized bed reactor, by forming a multi-stage fluidized bed with a temperature distribution in which the temperature inside the reactor is lowered sequentially from the bottom to the top, then thereby the temperature of the reaction gas flowing up in the reactor is gradually lowered as the reaction proceeding, It makes possible to increase the conversion ratio to methane at the reactor outlet.

3. In the temperature range above 300° C., where the amount of reaction heat is large, inorganic powders of chemical heat storage agents can be used as a fluidizing medium to enhance the heat removal capacity in this temperature range by mixing and using magnesium hydroxide which dehydrates above 300° C. and magnesium carbonate which decarbonates above 400° C.

4. Since magnesium oxide obtained by these dehydration and decarbonation is a chemical heat storage agent, the heat absorbed in the methanation reaction can be recovered and used as heat during regeneration, in which the hydration reaction is followed by the carbonation reaction. That is, it is possible to minimize the energy loss that occurs when converting the energy of hydrogen into methane.

Here, according to the rough calculation in FIG. 11, the powder receives the reaction heat from the rising gas when the powder of inorganic materials is flowing down in the multi-stage fluidized bed, on the other hand, when the gas rises in this multi-stage fluidized bed, it contacts with the powder to give its reaction heat, that is, these exchanges heat each other. However, in the above heat calculation, the heat exchange between the sensible heat of temperature rising of the powder side and the sensible heat of temperature lowering of the gas side are not considered. In order to verify the soundness of the present invention, it is necessary to conduct calculations with the consideration of the sensible heat of the temperature rising of the powder and the sensible heat of the temperature lowering of the gas in addition to the exchange of reaction heat.

Of course, in calculations that include these sensible heats, it is necessary to take into account not only the components involved in the reaction, but also the sensible heat of endothermic agents that are not involved in the reaction and the sensible heat of gas components that are not involved in the reaction.

Therefore, for the following three cases of A to C, composition change of each component in each temperature range, reaction amount and reaction heat at that time, temperature change and its sensible heat during temperature rising of flowing down powder, temperature lowering of ascending reaction gas and its sensible heat during temperature drop, etc. should be considered. Then, including above consideration, it was verified by calculating the change in the composition of each component and the transfer of heat between each component whether the exothermic and endothermic can be balanced as expected.

A. When supplying carbon dioxide from gas cylinders, etc.,

B. When using flue gas directly as a source of carbon dioxide,

C. When magnesium carbonate powder is used as a source of carbon dioxide

The calculation results for these three cases are described below. Note that this heat calculation does not take into consideration the difference in reaction rate between the gas side and the chemical heat storage agent, nor does it take into account heat loss such as heat radiation from the device.

The thermal calculation results are described below. In FIGS. 12-15, the right side shows the composition change and exothermic heat of the gas side (carbon dioxide, hydrogen, methane, water vapor) that is the heat generation side, and the left side shows the same of the heat absorption side, the change in the composition of inorganic powders (magnesium oxide, magnesium hydroxide and magnesium carbonate) and the value of the endothermic amount. In these calculations, magnesium oxide is used as the powder that does not involve in the reaction, but sand, silica, or the like may be used as the heat-absorbing material, as described above.

FIG. 12 shows changes in composition for the simplest case of supplying carbon dioxide from a gas cylinder or a gas tank.

Here, the heat generated by the methanation reaction in the temperature range above 300° C. is absorbed by the heat of the dehydration reaction of magnesium hydroxide. That is, no magnesium carbonate is used. In this calculation, the reactor consists of two stages, the upper stage (140-300° C.) and the lower stage (300-400° C.). The small tables in FIG. 12 show compositions of gas and inorganic powder after reaction proceeded in each reaction stage.

In this heat calculation, when the heat of reaction and sensible heat are calculated separately, the temperature range of the lower stage of the reactor is 300 to 400° C., but in the calculation of the reaction heat, the enthalpy changes were calculated by using the values at 350° C. as the median value of this range. As the temperature change in this region when the temperature rises or falls is 100° C., each sensible heat was obtained from each composition and enthalpy value at 300° C. and 400° C.

The upper stage of the reactor has a temperature range of 140 to 300° C., but the representative temperature for calculating the reaction heat is assumed to be 200° C. here, and the temperature change of rising or falling in this region is 140 to 300° C. Therefore, the temperature change was set to 160° C.

1 kmol of carbon dioxide and 4 kmol of hydrogen required for the methanation reaction are supplied into the reactor from the bottom of the reactor as shown in the lower right of FIG. 12. When these reaction gases are directly supplied at room temperature (25° C.), the temperature inside the reactor decreases, so its temperature was raises to 400° C. by exchanging heat with the 400° C. high-temperature powder extracted from the reactor in advance. That is, hydrogen was preheated and fed into the reactor.

The followings are the calculation results under these conditions. On the powder side, a mixed powder of 2.08 kmol of magnesium hydroxide powder as endothermic materials and 4.01 kmol of magnesium oxide powder was fed from the top of the reactor at 140° C. The powder whose reaction was completed during flowing down is extracted from the bottom of the reactor and sent to the regeneration process after preheating the feed gas as described above.

In the temperature range of 140 to 300° C., the powder fed from the top of the reactor does not occur dehydration, that is, does not change in the composition, and absorbs sensible heat from the gas to raise its temperature only.

In the next stage which temperature range is 300 to 400° C., it is assumed that 80% of the fed 2.08 kmol magnesium hydroxide is dehydrated, and the remaining 20% of 0.416 kmol magnesium hydroxide does not react. (This is just an assumption for trial calculation, and it is desirable to use the actual dehydration ratio confirmed by experiments.) Therefore, this 0.416 kmol magnesium hydroxide is extracted from the bottom of the reactor as 5.674 kmol magnesium oxide, which is a summation of the fed 4.01 kmol and produced 1.66 kmol by the dehydration reaction. The amount of water vapor generated by this dehydration is 1.66 kmol, and this water vapor rises together with the reaction gas.

Next, the calculation result of gas side will be explained.

1.0 kmol of carbon dioxide and 4.0 kmol of hydrogen enter into the temperature range of 300 to 400° C. of the lower stage of the reactor as the reaction gas at 400° C., and exchange its heat with the powder flowing down from the upper stage, then its temperature reaches to 300° C. and flow into upstairs. At this time, the equilibrium conversion ratio of the methanation reaction is 0.89 from FIG. 2. However, since actual conversion ratio of this reaction does not reach to the equilibrium conversion ratio within the actual residence time of the fluidized bed, here this equilibrium conversion ratio was assumed to reach to 85% of the equilibrium ratio.

As a result, the compositions of the gas side after the reaction is methane=0.77 kmol, carbon dioxide=0.23 kmol, water=1.54 kmol, and hydrogen=0.92 kmol. And these are shown on the lower part of the heat generation side on the right hand of FIG. 12.

Next, in the temperature range of 140-300° C., the conversion to methane was assumed to increase from 0.85 to 0.98. Therefore, the gas composition at the reactor outlet is methane=0.98 kmol, carbon dioxide=0.02 kmol, water=3.62 kmol, and hydrogen=0.08 kmol.

The magnesium oxide powder that does not involve the reaction works as an endothermic agent that absorbs sensible heat from the reaction gas when flowing down inside of the reactor.

Here, considering the temperature of the powder after regeneration treatment, the temperature of the powder fed into the top of the reactor is assumed to be 140° C.

If it is lower or higher than this, it can be adjusted by decreasing or increasing the amount of magnesium oxide powder to be fed.

Next, FIG. 13 shows the result of this trial calculation of the amount of heat transfer obtained from the temperature change and the enthalpy change of each component based on the composition change in FIG. 12. Numerical values in brackets [ ] in FIG. 13 indicate the amount of heat in MJ (Mega Joule). The transferring of heats in the reactor are described below from the bottom of the reactor.

Hydrogen is directly heat-exchanged with a mixed powder of 6.09 kmol of magnesium oxide and magnesium hydroxide at 400° C. extracted from the bottom of the reactor in the countercurrent contact method such as in a moving bed, and it receives the heat of 60 MJ to preheats it to 400° C. and feeds it to the bottom of the reactor. On the other hand, the mixed powder is sent to the regenerating process after the temperature is lowered from 400° C. to 288° C. by this heat exchanging. (Actually, a temperature difference of at least several degrees Celsius is required between the powder on the heating side and the gas on the heated side, but this temperature difference is assumed to be zero here because it is an approximation.)

The reaction gas at 400° C. entering the lower stage of the reactor reacts to produce methane whose conversion ratio is 77%, then exothermic 144 MJ of heat.

This heat is given to the mixed powder of about 300° C. flowing down from the upper stage of the reactor. Furthermore, by giving its own sensible heat of 19 MJ during temperature dropping to the powder (this heat is absorbed by the powder), while the temperature of the reaction gas itself is falling to 300° C., the gas flows up in the reactor to enter the 300° C. region of the upper stage of the reactor.

On the other hand, the mixed powder at 300° C. that enters from the upper stage of the reactor to the lower stage of the reactor raise its temperature by absorbing and exchanging the sensible heat of 37 MJ of the reaction gas when the temperature of the reaction gas is falling down and the reaction heat of the methanation at the lower stage of the reactor. That is, at this time, magnesium hydroxide of 1.66 kmol absorbs 127 MJ of dehydration heat from the reaction gas, then converts into magnesium oxide by dehydration, and further rises to 400° C. To summarize the above, in the lower stage of the reactor, the amount of heat given to the powder from the reaction gas is, as shown on the right side of the figure,

[Amount of heat given from gas to powder]=Exothermic reaction heat of gas+Sensible heat during gas temperature dropping down=144+19=163 MJ.

As the amount of heat that the powder receives from the gas is as shown on the left side of FIG. 13,

[Amount of heat received by powder from gas]=Endothermic reaction heat+sensible heat of powder for temperature rising=127+37=164 MJ.

At this time, these two values are almost equal, and the (exothermic heat+the sensible heat during gas temperature dropping) and (endothermic heat+the sensible heat of powder temperature rising) offset each other, so under this reaction condition, heat transfer tubes for heat removal is not required to maintain the temperature as constant, and any temperature change does not occur in the lower stage of the reactor.

Next, the heat transfer in the upper stage of the reactor will be explained in the same way.

Here also, the inorganic powder flowing down the inside of the reactor and the reacting gas rising up exchange their heats through countercurrent contact.

The reaction gas at 300° C. entered the upper stage from the lower stage of the reactor, here carbon dioxide further reacts up to 98%, releasing 31 MJ of heat, and giving heat of 31 MJ to the flowing down inorganic powder of magnesium oxide and magnesium hydroxide, then its temperature drops to 140° C.

On the other hand, the mixed powder at 140° C. feeding into the upper part of the reactor receives 62 MJ which is summation of the methanation reaction heat of 31 MJ and 31 MJ of sensible heat which is released from the reaction gas when the temperature of the reaction gas is lowering from 300° C. to 140° C., then the temperature of the powder rises up to 300° C. by receiving this heat. Namely,

[Amount of heat given by gas to powder]=exothermic heat+sensible heat of gas temperature dropping=31+31=62 MJ.

[Amount of heat that the powder receives from the gas]=The amount of heat for temperature rising of powder=62 MJ.

These two amount of heats become equal, Here also, the amount of heat generated is offset by the amount of heat absorbed, the temperature in the upper stage of the reactor does not change and a constant temperature can be maintained is indicated.

The above calculation does not include the heat removal by the heat removal heat transfer tubes inserted inside the fluidized bed.

Actually, instead of relying only on heat removal by the chemical heat storage material, it is also possible to control the internal temperature in combination with heat removal by heat transfer tubes in order to increase the ability to respond to various disturbances in the process. When a heat-removing using heat transfer tube is also used, the amount of inorganic powder fed corresponding to the amount of heat removed by the heat transfer tube may be reduced for adjustment.

By the way, in FIGS. 12 and 13, in order to simplify the heat calculation, the inside of the reactor was explained as having a two-stage structure, an upper stage and a lower stage.

However, this is not necessarily limited to a two-stage configuration, and of course it can be allowed to be a configuration with more stages.

Next, FIG. 14 shows the relationship between changes in composition and transfer of heat, similar to FIGS. 12 and 13, when it is assumed that flue gas is directly supplied into the reactor as a supplying source of carbon dioxide. However, the composition change and the transfer of heat are summarized in one table. That is, the numerical values in the small tables indicated by the solid line in each stage indicates the composition of the each component in each reaction field, like as in FIG. 12. And, small numerical values indicated by broken lines in the table indicate amounts of reaction heat and sensible heat, like as in FIG. 13.

Here, the temperature of flue gas used is 140° C. The composition is shown at the bottom of FIG. 14, and was assumed to be carbon dioxide=1 kmol, water vapor=2.5 kmol, nitrogen=5.0 kmol, and residual oxygen=0.25 kmol.

To avoid introducing residual oxygen in the flue gas into the methanation reactor, a stoichiometrically equivalent amount of hydrogen to the residual oxygen is used to pre-combust to water vapor. The gas composition after this oxyhydrogen combustion becomes carbon dioxide=1 kmol, water vapor=3.0 kmol, and nitrogen=5.0 kmol.

At this time, the combustion heat due to oxyhydrogen combustion is 123 MJ, and 74 MJ of this heat is consumed to raise the flue gas temperature from 140° C. to 400° C.

In addition, the 4 kmol hydrogen that is supplied to the methanation reaction receives 44 MJ of heat from this combustion heat, and similarly rises to 400° C. After deducting these, the remaining surplus heat is 5 MJ, but this amount of heat is carried from the bottom of the reactor to the lower stage of the reactor together with the flue gas and hydrogen. Actually, this heat of 5 MJ makes the supplied gas temperature raise from 400° C. by only a few degrees.

On the gas side, in the lower stage of the reactor, the reaction gas reacts to become methane=0.8 kmol, carbon dioxide=0.2 kmol, water vapor=4.60 kmol, hydrogen=0.8 kmol, nitrogen=5.0 kmol. On the other hand, 80% of the 2.34 kmol magnesium hydroxide in the powder proceeds a dehydration reaction, releasing 1.87 kmol water vapor. The amount of magnesium oxide is 10.25 kmol by adding 8.38 kmol and 1.87 kmol. Also, unreacted magnesium hydroxide is 0.468 kmol.

The heat transfer in the lower stage of the reactor is calculated based on the above composition change, adding the reaction heat of the reaction gas 144 MJ, the sensible heat of temperature dropping of the gas 52 MJ, and the heat amount of 5 MJ brought in by the reaction gas. That is, the total amount of heat is 144+52+5=201 MJ, and this amount of heat is given to the powder flowing down from the upper stage of the reactor.

Here, the amount of heat absorbed when 1.87 kmol of magnesium hydroxide is dehydrated is 143 MJ, and the amount of heat required to raise the temperature of the mixed powder to 300-400° C. is 58 MJ. The sum is 143+58=201 MJ, where the heat release is also offset by the heat absorption. To summarize the above, in the lower stage of the reactor,

[Amount of heat given by gas to powder]=(gas reaction heat+gas temperature lowering sensible heat+oxyhydrogen combustion surplus heat)=144+52+5=201 MJ,

[Amount of heat received by powder from gas]= (sensible heat of temperature rising of mixed powder)=143+58=201 MJ Namely, the exothermic heat is offset by the endothermic value.

Likewise for the upper stage of the reactor, each composition change is shown in the figure, and the transfer of heat based on this composition change is

[Amount of heat given to powder from gas]=(reaction heat of gas+sensible heat of gas temperature dropping)=31+67=98 MJ,

[Amount of heat received by powder from gas]= (sensible heat of temperature rising of mixed powder)=98 MJ, So, the exothermic heat is canceled by the endothermic heat. As described above, it shows that by using the flue gas containing carbon dioxide from which the residual oxygen in the flue gas has been previously removed is used as the raw material gas for the methanation reaction, synthesizing of methane with hydrogen is possible in terms of heat calculation.

Here, in the process of absorbing carbon dioxide gas by the amine method that directly supplies flue gas, when the flue gas is directly supplied to the amine absorption process, the amine absorption liquid may deteriorate by the small amount of SOx component. Since the present invention does not use an amine-based absorbing liquid, there is no such concern. For the concern that the catalyst used for the methanation reaction will be poisoned by a small amount of SOx components in the flue gas. However, in the present invention, there is overwhelmingly larger amount of magnesium hydroxide and magnesium oxide than that of catalyst, which are also desulfurizing agents. Therefore, SOx is converted into MgSO4 and is considered to be rendered harmless.

As the third case, FIG. 15 assumes that the carbon dioxide released by the decarbonation reaction of magnesium carbonate is used as the supplying source of carbon dioxide. Similarly, from this results of thermal calculations. The reaction conditions under which the amount of heat generated and the amount of heat absorbed at each stage can be offset each other is shown based on the composition change of each inorganic powder component and heat calculation.

Here, magnesium carbonate obtained by carbonation of magnesium hydroxide is usually basic magnesium carbonate, In terms of thermal calculation, its chemical composition can be regarded as a mixture of magnesium hydroxide and magnesium carbonate, so this trial calculation treats it as a mixture of these.

The main difference points between FIGS. 12-14 is that in this thermal calculation, the inside of the reactor is composed of three stages (upper, middle, and lower).

The temperature at the bottom of this reactor is the temperature region of 400 to 500° C., at which the decarbonation reaction proceeds.

In this case, the heat of the methanation reaction alone is insufficient to obtain a high temperature above 400° C. Here, it is assumed that the insufficient amount of heat is made up by oxyhydrogen combustion with air, and using the combustion heat to make up for raising the temperature to 500° C. That is, 25° C. air (0.14 kmol $O_2$, 0.56 kmol $N_2$) and 0.28 kmol hydrogen are oxyhydrogen-combusted, and the combustion heat at that time can raise the gas temperature to 500° C. Of course, if the temperature of the source gas hydrogen can be raised by other preheating means, this oxyhydrogen combustion becomes unnecessary.

The calorific value of this oxyhydrogen combustion is 69 MJ, the heat required to raise the temperature of air from 25° C. to 500° C. is 13 MJ, and the amount of heat required to raise the temperature of 4 kmol hydrogen for the methanation is 56 MJ, and when the gas heated to 500° C. by this combustion heat is brought into the 400-500° C. region at the bottom of the reactor, the excess heat is 55 MJ. Again, this excess heat actually raises the temperature of the feed gas to over 500° C. When this oxyhydrogen combustion is occurred in the lowermost stage of the reactor, the decarbonation reaction (endothermic reaction) is carried out at the same time by the heat generated from the hydrogen combustion, so an excessive rise in temperature can be prevented.

Next, in this 400-500° C. region, the equilibrium conversion ratio of the methanation reaction is about 70%. Assuming that the actual reacted ratio to methane is 70%, that is, 49%, the calorific value is 91 MJ. The gas composition at this time is as described in the small table. Furthermore, the amount of heat (sensible heat of temperature dropping) when this reaction gas is lowered from 500° C. to 400° C. is 19 MJ, so in the lower stage of the reactor,

[The amount of heat given to the powder from the gas]=The amount of heat brought in by the gas+the reaction heat+the sensible heat of temperature dropping=55+91+19=165 MJ.

On the other hand, the input amounts of the mixed powder as the endothermic material are magnesium oxide=4.74 kmol, magnesium hydroxide=0.45 kmol, and magnesium carbonate=1.0 kmol.

In this lowermost stage, the temperature is higher than that in the middle part, so all magnesium hydroxide has been already dehydrated and changed to magnesium oxide, and the respective amounts are magnesium oxide=5.19 and magnesium carbonate=1.0 kmol. The amount of heat required to raise the temperature of this mixed powder to 400-500° C. is 51 MJ, and the amount of heat required to completely decarbonate 1 kmol of magnesium carbonate is 114 MJ, then,

[The amount of heat that the powder receives from the gas]=Endothermic reaction heat+Powder temperature rising sensible heat=114+51=165 MJ Again, the amount of heat generated is offset by the amount of heat absorbed. (Also here, of course, the reaction rate of magnesium carbonate may be 50% or 80%. For example, when the reaction rate is 50%, the amount of magnesium carbonate to be fed is doubled, And the amount of heat absorption can be adjusted by reducing the amount of magnesium oxide corresponding to the amount of sensible heat of magnesium carbonate that is unreactable component.)

In this 400-500° C. range, the carbon dioxide released by decarbonation from magnesium carbonate becomes the raw material gas for the methanation reaction, so this gas flows upward in the reactor together with other gases while reacting with hydrogen.

Next, in the middle stage of the reactor, the compositions of the gas side and the powder side are as shown in FIG. 15. Based on these composition changes, on the gas side, methanation reaction heat=54 MJ,
gas temperature dropping sensible heat=17 MJ,
and the sum of them is 71 MJ.

[Heat given to powder by gas]=heat of exothermic reaction+sensible heat of gas temperature dropping=54+17=71 MJ.

On the powder side, heat of dehydration reaction of 0.45 kmol magnesium hydroxide=34 MJ,
heat of temperature rising of the powder=37 MJ,
and the sum of them is 71 MJ.

[The amount of heat received by the powder from the gas]=Endothermic reaction heat+Sensible heat of the powder=34+37=71 MJ Here also, the amount of heat generated is offset by the amount of heat absorbed. Water vapor of 0.45 kmol is released and rises in the reactor together with the reaction gas.

Finally, similarly in the uppermost stage of the reactor,

The heat of methanation reaction is 31 MJ, the sensible heat of temperature dropping of the gas is 27 MJ, and the sum of them is

[The amount of heat given to the powder by the gas]=Heat of exothermic reaction+Heat of sensible heat of temperature drop=31+27=58 MJ And this value is equal to 58 MJ of heat required to raise the temperature of the powder at 140° C. to 300° C.

[The amount of heat received by the powder from the gas]=Sensible heat of the powder=58 MJ Therefore, even in this case, the amount of heat generated is offset by the amount of heat absorbed in each stage in the reactor, and the temperature in the reactor can be stabilized.

In the case shown in FIG. 15, the magnesium carbonate powder is used after mixing it with the inorganic powder that is the fluidizing medium of the methanation reactor. This magnesium carbonate can be obtained by reacting magnesium oxide with carbon dioxide in the flue gas. It means that methane is produced by using carbon dioxide gas obtained once converting into magnesium carbonate and then decarbonating it in a methanation reactor as a raw material. That is, this is one of the CCUS technologies.

As described above, in FIGS. 12-15, in three cases where the supply sources of carbon dioxide as the raw material are different, without heat transfer tubes for heat removal, the exothermic heat in the methanation reactor can be completely offset by input the chemical endothermic material adjusted their compositions and amounts. That is, it was shown that the temperature in each stage in the multi-stage fluidized bed can be controlled to be constant without using heat transfer tubes for heat removal.

Of course, cases other than these three can be assumed, but in any case, the amount of heat absorption can be adjusted by adjusting the amount and ratio of each powder of magnesium oxide, magnesium hydroxide, and magnesium carbonate. The temperature in each temperature region in this type of reactor can be kept constant without heat transfer tubes for heat removal.

Now, in the above trial calculation, the reaction rate of the powder, the methanation reaction rate, and the residence time (=reaction time) of each are not taken into account. In the following, taking these into account, how to match the amount of heat absorbed and the amount of heat generated in each fluidized bed will be shown.

In general, the reaction speed of gas is fast, the burning speed of gas is a typical example. Conversely, since the reaction rate of powder is that of a solid and depends on its specific surface area. So, if the particles are in the form of lump such as charcoal, the reaction rate is much slower than that of gas. In fact, according to Non-Patent Document 7, the dehydration reaction rate of magnesium hydroxide crystal powder is about 50 minutes (=3000 seconds) to reach a dehydration ratio of about 90% at around 350° C., this is considerably slower than that of gas.

On the other hand, regarding the residence times of the powder and gas in the fluidized bed, the specific volume of the gas is overwhelmingly larger than that of the powder when the powder and gas react with the same amount of mole. The flow velocity of gas becomes very high compared to that of powder flow, i.e. the residence time of the gas becomes very short compared to that of the powder.

As described above, the powder has a slow reaction rate but a long residence time, while the gas has a fast reaction rate but a short residence time.

The heat absorption and heat generation in each stage are proportional to the respective reaction amounts of the powder and gas, and the reaction amount is proportional to the product of the reaction rate and the residence time. So, heat balance in each stage should be discussed based on the value of the product of (=reaction amount).

Although rough estimation, the reaction amounts of the powder and gas in the fluidized bed are shown their results below with the consideration of the residence time.

Equation 4 is the relationship among the fluidized bed volume VFB, the fluidized bed cross-sectional area S, and the fluidized bed height $H_{FB}$ for one stage of fluidized bed in the multi-stage fluidized bed. Since the fluidized bed contains the heat transfer tubes for heat removal and the catalyst, when those occupied volumes are $V_{tube}$ and $V_{cat}$, respectively, the volume of the actual fluidizing media occupied by the powder and the fluidizing gas, $V_{fpg}$, is given by Equation 5. Here, when the porosity ratio in this $V_{fpg}$ is ε, the occupied volume $V_{fp}$ of the powder in this $V_{fpg}$ is expressed on the left part of right side of Equation 6, and the occupied volume $V_{fg}$ of the fluidizing gas is expressed on the right part of right side of Equation 6.

Here, the powder continuously flows into $V_{fp}$, which is the volume occupied by the powder in the fluidized bed, at a molar flow rate of $Q_p$, stays at an average residence time of $\tau_p$, and then leaves at a rate of $Q_p$. Here, since the powder flowing into this fluidized bed contains $Q_{Rp}$ and $Q_{ip}$ in molar flow rates of substances involved in the reaction and substances not involved in the reaction, respectively, the molar flow rate $Q_p$ of the powder is the sum of these two, (the left side of Equation 7). On the other hand, the gas side also contains gas components that react and gas components that are not involved in the reaction. The molar flow rate $Q_g$ is the sum of them and is expressed on the right side of Equation 7.

Here, the powder $Q_{Rp}$ involved in the reaction are magnesium hydroxide or magnesium carbonate when a magnesium-based compounds are used as the chemical heat storage agent. And $Q_{ip}$ as a substance not involved in the reaction is magnesium oxide which is produced by the heat absorption reaction.

The gas $Q_{rg}$ involved in the reaction means carbon dioxide and hydrogen, and the gas $Q_{ig}$ not involved in the reaction are nitrogen when nitrogen is contained in the input gas, and methane or water vapor as a reaction product.

Regarding Equation 8, the left side shows the reaction formula of the powder, and the right side shows the reaction formula of the methanation reaction of gas. The stoichiometric coefficients of each component are shown below of each reaction formula. Since the dehydration reaction is shown here, the water vapor of 1 kmol generated by the dehydration reaction of 1 kmol should be added to the molar flow rate after the reaction of the gas side, and the molar flow rate of this water vapor is shown as (1) by parentheses in equation 8. In the case of the decarbonation reaction, all of the generated carbon dioxide is consumed as the raw material gas for methanation.

$$H_{FB} = \frac{V_{FB}}{S} \qquad \text{[Equation 4]}$$

$$V_{fpg} = (V_{FB} - V_{tube} - V_{cat}) \qquad \text{[Equation 5]}$$

$$V_{fp} = V_{fpg}(1 - \varepsilon), \; V_{fg} = V_{fpg}\varepsilon \qquad \text{[Equation 6]}$$

$$Q_p = Q_{ip} + Q_{rp}, \; Q_g = Q_{ig} + Q_{rg} \qquad \text{[Equation 7]}$$

$$Mg(OH)_2 \rightarrow MgO + H_2O\uparrow, \quad \begin{matrix} CO_2 + 4H_2 \rightarrow CH_4 + \\ 2H_2O(+H_2O) \end{matrix} \qquad \text{[Equation 8]}$$

$$1 \rightarrow 1 + (1), \qquad [1 + 4 = 5] \rightarrow [1 + 2 = 3](+1)$$

The respective volumetric flow rates $U_p$ and $U_g$ of the powder and gas through this fluidized bed are determined by multiplying this molar flow rate by their respective specific volume $v_p$ and $v_g$. Here, when the molar specific volumes change before and after the reaction, the average value before and after the reaction is used, and these average values are $v_{p(av)}$ and $v_{g(av)}$, respectively. Therefore, the volumetric flow rate of powder is $U_{p(av)}$ on the left side of Equation 9, and the volumetric flow rate of gas $U_{g(av)}$ is on the right side of Equation 9. Using these, the time to pass through the fluidized bed, that is, the residence times $\tau_p$ and $\tau_g$ are calculated by dividing the occupied volume in the fluidized bed by the volumetric flow rate to obtain Equation 10, and substituting Equations 6 and 9 into Equation 10 respectively, Equations 11 and 12 are obtained. So, the relational equations of the residence time of the powder and the gas in the fluidized bed are obtained.

Here, comparing to the number of moles of the powder reacting, the number of moles of the gas is 5 moles before the reaction and 3 moles after the reaction from Equation 8. So, when the average value is 4 moles in this calculation, since the ratio of the molar flow rate of powder and gas is given by Equation 13, the ratio of $\tau_p$ to $\tau_g$ is given by Equation 14.

$$U_{p(av)} = Q_p \times v_{p(av)}, \; U_{g(av)} = Q_g \times v_{g(av)} \qquad \text{[Equation 9]}$$

$$\tau_P = \frac{V_{fp}}{U_{p(av)}}, \; \tau_g = \frac{V_{fg}}{U_{g(av)}} \qquad \text{[Equation 10]}$$

$$\tau_P = \frac{V_{fp}}{U_{p(av)}} = \frac{V_{fpg}(1 - \varepsilon)}{Q_p \times v_{p(av)}} \qquad \text{[Equation 11]}$$

-continued $$\tau_g = \frac{V_{fg}}{U_{g(av)}} = \frac{V_{fpg}\varepsilon}{Q_g \times v_{g(av)}}$$ [Equation 12]

$$4Q_{rp} \approx Q_{rg(av)}$$ [Equation 13]

$$\frac{\tau_P}{\tau_g} = \frac{U_{g(av)}}{U_{p(av)}}\frac{(1-\varepsilon)}{\varepsilon} = \frac{Q_g \times v_{g(av)}}{Q_p \times v_{p(av)}}\frac{(1-\varepsilon)}{\varepsilon} \approx 4\frac{v_{g(av)}}{v_{p(av)}}\frac{(1-\varepsilon)}{\varepsilon}$$ [Equation 14]

Here, when comparing using the molar standard specific volumes of magnesium oxide as the inorganic powder and gas, the molar specific volume $v_p$ of magnesium oxide is about 0.011 [L/mol] from the value of its true density. The molar specific volumes of magnesium hydroxide and magnesium carbonate are 0.025 [L/mol] and 0.028 [L/mol], respectively. On the other hand, the molar volume $v_g$ of the gas is about 50 [L/mol] when it is an ideal gas state at 400° C., so the ratio is about 4500 to 1800 times. Therefore, in the following calculation, below examination is carried out by adopting 3000 times as this average value as shown in Equation 13.

In general, the porosity ratio e of particles with good fluidity is assumed about 0.3, and the value of $(1-\varepsilon)/\varepsilon$ at this time is about 2.3 as shown on the right part of Equation 16, so these values are substituted into Equation 14. Then, the ratio $\tau_p/\tau_g$ of the average residence time of the powder and the gas passing through the fluidized bed is about 28,000 as shown in Equation 17. That is, in the methanation reactor, it means that the residence time (=passage time) of the gas is overwhelmingly smaller than the residence time of the powder passing through the fluidized bed.

$$\frac{v_{g(av)}}{v_{p(av)}} \approx 3,000$$ [Equation 15]

$$\varepsilon \approx 0.3, \frac{(1-\varepsilon)}{\varepsilon} \approx 2.3$$ [Equation 16]

$$\frac{\tau_P}{\tau_g} \approx 28,000$$ [Equation 17]

In a fluidized bed at 350° C., when the residence time of magnesium hydroxide powder is 3000 seconds, the dehydration ratio reaches about 90% during this time. However, the residence time of gas passing through this fluidized bed is only about 0.11 seconds. When the gas reaction reaches a reaction amount (=heat generation) equivalent to 90% of the heat absorption of the dehydration reaction of magnesium hydroxide existing here within this 0.11 second, the heat absorption and heat generation become equal. That is, the reaction temperature does not rise or fall, and keeps constant.

However, although the reaction rate of the gas is fast, there is a concern that the residence time may be too short at 0.11 seconds. Therefore, when these two do not match (when the residence time of the gas is too short, or when the reaction amount (exothermic heat) of the gas is larger than the endothermic reaction amount), how to deal with the matching is shown below.

When the residence time of the gas is short and the reaction amount on the gas side is smaller than expected, the exothermic heat decreases, but on the other hand, the endothermic reaction of the powder does not proceed unless heat is given, and as a result, the reaction amount of the powder is equal to the reaction amount of the gas.

Conversely, if the reaction amount of the gas is larger than the reaction amount of the powder, the heat absorption amount will be insufficient for the heat generation amount, so the temperature will rise. However, as shown in FIG. 2, the temperature rising of the reaction field leads to a decreasing in the equilibrium conversion ratio, and a reverse reaction (steam reforming reaction, which is an endothermic reaction) corresponding to this decreasing of conversion ratio occurs, as the result, the exothermic heat of the gas is suppressed to balance.

Based on the above consideration, when the powder supplying rate $Q_p$ and the gas supplying rate $Q_g$ are constant, the reaction amount of the gas in each stage of the fluidized bed is given by the product of the reaction rate of the gas and the residence time $\tau_g$, in addition, the reaction rate can be adjusted by the amount and activity of the catalyst in the fluidized bed. On the other hand, the gas residence time $\tau_g$ (=passage time through the fluidized bed) is proportional to the fluidized bed height $H_{FB}$ and the fluidized bed porosity ratio $\varepsilon$ according to Equations 4-12.

When the fluidized bed height which gives the residence time $\tau_g$ required to obtain the desired gas reaction amount in each fluidized bed is $H_g$, and similarly the fluidized bed height which also gives the residence time $\tau_p$ necessary to obtain the desired powder reaction amount is $H_p$, furthermore when the condition is $H_p > H_g$ (that is, it means that the reaction rate of the gas is fast), the reaction amount of the powder cannot exceed the reaction amount of the gas as described above. Since both amounts result equal, the fluidized bed height can be set to a height $H_p$ that gives a required reaction amount of the gas, that is, $H_{FB} = H_p$.

On the other hand, when $H_p < H_g$, the height of the fluidized bed must be $H_g$ in order to obtain the desired gas reaction amount, that is, $H_{FB} = H_g$. However, at this time, the supply amount $Q_p$ of inorganic powder (2.08 kmol magnesium hydroxide and 4.01 kmol magnesium oxide in the example of FIG. 12) and the supply amount $Q_g$ of gas (carbon dioxide 1.0 kmol and hydrogen 4.0 kmol) should not be changed. This is because the amount of heat absorbed by the powder and the amount of heat generated by the gas are defined by these $Q_p$ and $Q_g$ regardless of the amount of powder present (holdup amount) in the fluidized bed. In other words, at this time, $H_{FB}$ becomes higher than $H_p$ (although the retention time $\tau_p$ of the powder becomes longer than the required time), the amount of heat absorbed by the powder cannot increase beyond the amount of heat generated by the gas, so there is no problem.

The height of the fluidized bed may be adjusted by adjusting the height of the down corner weir (21 in FIG. 5) at each stage. Of course, it is also effective to adjust the supply amount of the reaction gas to balance the amount of heat against the disturbance during plant operation.

Next, $H_{FB}$ can be increased to obtain the required amount of gas reaction, in the examples in FIGS. 12-15, the temperature difference between each stage is set to 100° C. to simplify the calculations. Considering thermal strain and the like in an actual device, that this temperature difference is preferable smaller. Therefore, for example, by dividing a fluidized bed with a temperature difference of 100° C. into four stages and setting the temperature difference between each stage to 25° C., the thermal strain of the equipment can be greatly reduced. Further, increasing the number of stages is preferable because the flow property of powder in the multi-stage fluidized bed becomes closer to plug flow. The above knowledge should be reflected in the design of the apparatus.

Here, the reaction rate of powder depends on its specific surface area. Therefore, when the particle size is large, the reaction rate would decrease. Therefore, it is preferable to use fine powder or to use porous particles obtained by granulating fine powder. However, a fluidized bed using fine powder tends to cause drift, and it is generally considered difficult to fluidize fine powder. In order to enable fluidization of the fine powder and uniform treatment of the powder, it is preferable to use a multi-stage fluidized bed using the swinging mechanism of Patent Document 2.

At this time, in the fluidized bed using fine powder, the bed height of the fluidized bed tends to expand due to uniform fluidization, and this expansion of the bed increases the porosity ratio in the bed, so the gas residence time increases. On the other hand, since the volume occupied by the powder is reduced, the residence time of the powder tends to be shortened. So, such care must be taken not to shorten it too much.

Next, the attention for changing in properties accompanying powder reactions should be paid. Namely, when the reaction progresses to 100%, all the substances are changed to different other substances. In other word, the true specific gravity of the particles changes, and as a result, changes in particle properties such as changes in particle size occur. Therefore, when the dehydration and decarbonation reactions of the powder and their regeneration are repeated, it is conceivable that these property changes affects the operating conditions such as the handling of the powder. In order to suppress the influence of such property changes on the flow characteristics of the powder, powder processing such as encapsulating the powder with a non-reactive substance such as silica is conceivable. The simplest way may be to limit the reaction rate to 50% or 30% without such processing.

The example in FIG. 15 is a trial calculation when 1 kmol of magnesium carbonate is reacted up to 100%. If this is set to 50%, the amount of heat removed in the 400 to 500° C. range will be halved and will be insufficient. In this case, it is necessary to double the amount of magnesium carbonate powder to be fed to 2 kmol and maintain the reaction amount in it to be 1 kmol. At this time, regarding of sensible heat, the value of sensible heat per mole of magnesium carbonate between 14° and 500° C. is about 2.3 times of the molar sensible heat of magnesium oxide. Therefore, since the amount of magnesium carbonate to be added is increased by 1 kmol, 2.3 kmol of magnesium oxide, which corresponds to this sensible heat, should be reduced from the amount of input of 4.74 kmol to 2.44 kmol.

The above trial calculations are merely desk calculations, and the actual temperature inside the reactor may vary due to various factors. In order to deal with these changes, it is preferable to control the amount of heat generated by adjusting the amount of supply of the reaction gas, because the response speed to the reflection of the conditions of the apparatus is fast. In addition, when the heat transfer pipes are installed for the purpose of partly removing heat, it is possible to adjust the amount of heat removed by the heat transfer pipes.

As described above, one of the major features of the present invention is that inorganic powders as fluidizing medium and chemical heat storage agents for the removal of methanation reaction heat are used, which are magnesium hydroxide and magnesium carbonate as endothermic above 300° C. and magnesium oxide. Since these powders do not change unless they come into contact with moisture or carbon dioxide, they can be stored stably for a long period of time (heat storage) under atmospheric pressure.

Therefore, if the magnesium oxide powder extracted and cooled from methanation reactor is transported to factories emitting flue gas containing carbon dioxide and stored in a silo. Magnesium oxide can be used to generate the heat required at when heat is required in these factories. At the timing when heat is required in these factories, taking out the required amount of magnesium oxide, hydration reaction in the regeneration process and further carbonation reaction, then the stored heat can be recovered and used during regeneration.

In general, the reason why the utilization rate of waste heat does not increase in factories is that the temperature, quantity and timing of waste heat released do not match the demands of temperature, quantity and timing of the processes that utilize it. However, at the peak of heat utilization in the factory, these powders are extracted and regenerated, and the heat generated at this time can be recovered and used for such as preheating boiler water or preheating boiler combustion air. That is, a portion of the heat usage of the factory can be compensated.

This means that the 17% energy lost when converting hydrogen into methane is not loss and can be effectively used elsewhere.

The features of the methanation reactor using the multi-stage fluidized bed of the present invention are summarized.

A. It improves the heat removal performance of the reaction heat generated in the reactor, suppresses the rise of the catalyst surface temperature, and contributes to the extension of the catalyst life.

B. Lowering the temperature in the multi-stage fluidized bed stepwisely from the bottom to the top of the reactor, furthermore, by selecting and using catalysts that are effective in each temperature range, a high conversion ratio to methane can be achieved without lowering the reaction rate even at the outlet of the reactor where the temperature is low. Then the residual hydrogen concentration can be reduced.

C. For a large amount of exothermic heat in the temperature range above 300° C. in the multi-stage fluidized bed, chemical heat storage agents such as magnesium hydroxide powder and magnesium carbonate powder that decompose and absorb heat are mixed into inorganic powder as fluidizing medium and uses it in this temperature range for heat removal by feeding it into the methanation reactor. These endothermic reactions greatly increase the heat removal capacity in this temperature range.

D. The magnesium oxide obtained from the dehydration reaction of magnesium hydroxide and the decarbonation reaction of magnesium carbonate can be regenerated and used, and the heat generated during this regeneration treatment can be recovered to use it. By using this recovered heat, it is possible to reduce the energy loss when converting hydrogen into methane.

E. Magnesium oxide, magnesium hydroxide, and magnesium carbonate are chemical heat storage agents, and can be stably stored and transported under atmospheric pressure as long as moisture and carbon dioxide are blocked. Then, the carbon dioxide in the flue gas of the factory, which is the source of carbon dioxide, reacts to form magnesium carbonate during regeneration treatment of magnesium oxide. Therefore, by fixing carbon dioxide in flue gas into magnesium carbonate and by transporting it to a methanation reactor, this carbon dioxide can be converted into methane to reuse.

F. Since magnesium carbonate reacted with carbon dioxide can be easily stored and transported under atmospheric pressure, even if the operation time and processing capacity of the carbon dioxide generation source and the methanation reactor do not match, in addition, even if the factories that are carbon dioxide sources are small and those locations are dispersed, after transporting the magnesium carbonate obtained from the flue gas of these facilities to the methanation reactor and storing collected whole of them. The carbon dioxide in the magnesium carbonate can be converted into methane by taking out required amount of it from the storage. That is, an efficient operation can be performed independently and separately without interfering with each other.

BRIEF DESCRIPTION OF THE DRAWINGS

FIG. 1 Relationship between the Gibbs free energy change ΔG and temperature of various reactions related in this process.

FIG. 2 Regarding the methanation reaction, the relationship between the conversion ratio of carbon dioxide to methane obtained from the equilibrium constant K calculated from ΔG and the temperature. The perpendicular bars in this figure are the conversion ratios in each stage of the multistage apparatus FIG. 3 A one-stage fluidized bed reactor equipped with heat transfer tubes for heat removal.

FIG. 4 A two-stage fluidized bed reactor equipped with heat transfer tubes for heat removal in which powder circulates between the reactor and an external cooler.

FIG. 5 Conceptual diagram of a multi-stage fluidized bed reactor equipped with a swinging mechanism and heat transfer tubes for heat removal.

FIG. 6 An example of arrangement of a honeycomb catalyst, a heat transfer tube for heat removal, and a swinging perforated plate in one stage in a multi-stage fluidized bed.

FIG. 7 Block flow diagram of the regeneration process, the left side is the process of regenerating a part of or all of magnesium oxide as magnesium hydroxide, and the right side is the process of regenerating a part of or all of magnesium hydroxide as magnesium carbonate FIG. 8 A moving bed equipped with a swinging mechanism used when regenerating magnesium oxide into magnesium hydroxide or when regenerating magnesium hydroxide into magnesium carbonate.

FIG. 9 Flows of chemical heat storage agents and heat when the chemical heat storage agents circulate between the methanation process and the chemical heat storage agent regeneration process.

FIG. 10 The conceptual diagram shown that a factory producing hydrogen from renewable energy, a methanation plant adjacent to this, transportation lines of the powder of magnesium carbonate containing carbon dioxide which is fixed it of flue gases of multiple factories, the carbon dioxide is provided to the methanation reaction, and the magnesium oxide from the methanation plant is recycled to the factories for regeneration of it.

FIG. 11 The reaction amount and reaction heat of the methanation reaction in two temperature ranges of 300 to 400° C. and 400 to 500° C., and the corresponding endothermic reaction and amounts of the endothermic heat of them.

FIG. 12 Shows changes in composition for the simplest case of supplying carbon dioxide from a gas cylinder or a gas tank.

FIG. 13 Shows the result of a trial calculation of the amount of heat transfer obtained from the temperature change and the enthalpy change of each component based on the composition change in FIG. 12.

FIG. 14 Shows the relationship between changes in composition and transfer of heat when it is assumed that flue gas is directly supplied into the reactor as a supplying source of carbon dioxide.

FIG. 15 Shows a trial calculation when 1 kmol of magnesium carbonate is reacted up to 100%.

EMBODIMENT FOR CARRYING OUT THE INVENTION

The possibility and features of the methanation reactor of the multi-stage fluidized bed using chemical heat storage agents have been described above. Hereinafter, the device realizing this function will be described.

The dehydration of magnesium hydroxide and hydration of magnesium oxide, and the decarbonation of magnesium carbonate and carbonation of magnesium hydroxide or magnesium oxide, these are chemical heat storage agents added to the fluidizing medium. These reactions are occurred on the solid surface. So, in order to increase the reaction rate and increase the residence time of the gas, it is preferable to use fine powder with a high specific surface area. However, fine powder is generally considered difficult to fluidize itself. Therefore, it is necessary to devise a way to realize uniform fluidization of fine powder.

In order to fluidize the fine powder, a vibrating fluidized bed is used in which the entire fluidized bed is vibrated up and down. Of course, this method can also be applied to this methanation reactor, but in the case of this system, since the vibrational energy is proportional to the mass and amplitude of the device, the larger the device is, the greater the energy required for vibration.

On the other hand, in the multi-stage fluidized bed using the swinging mechanism of Patent Document 2, only the powder inside is gently shaken without moving the device.

So, the amount of mass to be moved is considerably smaller than that of the vibrating fluidized bed system in which the entire apparatus is vibrated.

It is said that the preferable vibration frequency of the vibrating fluidized bed should be 5 to 50 Hz, but in the case of the swinging mechanism, the value is as small as about 0.01 to 1 Hz. Since the vibrational energy is proportional to the square of the frequency of vibration, it can be seen that the required energy for this swinging motion is overwhelmingly smaller comparing to the required energy for the vibrating fluidized bed.

As described above, from the viewpoint of required energy, in the methanation reactor of the present invention, it is preferable to use a multi-stage fluidized bed equipped with a swinging mechanism in order to enable fluidization of fine powder and uniform treatment of powder.

Next, FIG. 5 shows the concept of a methanation reactor using a multi-stage fluidized bed. In this figure, the fluidized bed has a four-stage structure, but this is not limited to a four-stage structure, and more than four stages may be used. In this figure, 140° C. inorganic powder is fed in the top stage, the temperature at the bottom is 400° C. or 500° C., and the intermediate temperature changes in stages.

In addition, in this figure, assuming that fine powder is used as the powder, the above-described swinging mechanism is used to assist uniform fluidization of the fine powder.

For this purpose, a motor 16 for driving the swinging mechanism, a drive shaft 17 for transmitting rotational motion to the swinging plate, and a perforated swinging plate 18 are shown.

When this swinging mechanism is used, in addition to averaging the bulk density of the powder in the bed, the powder entering on the dispersion plate from the powder supplying port 15 is spread over the entire surface of the dispersion plate and leveled as smooth by using the swinging motion of the swinging perforated plate 18.

Also, here, it is assumed that the catalyst 19 having a large particle size is used and is rolled on the dispersion plate by the movement of the swinging plate. The reason why the catalyst particles 19 in this figure have a large particle size is that they remain in the fluidized bed of each stage without being fluidized in the powder by the fluidizing gas. Of course, when using a molded body such as a honeycomb, the rolling of the catalyst is not necessary.

FIG. 6 shows an image of the layout of the catalyst, heat transfer tubes for heat removal, and perforated swinging plate in the bed, taking out only one stage of the multi-stage fluidized bed in such a case.

The powder enters the lower fluidized bed through the downcomer 20 from the upper fluidized bed.

Here, a honeycomb-shaped catalyst 19 is fixed under the heat transfer tubes 5 for heat removal. The reaction gas proceeds the reaction on the surface of the catalyst when passing through the honeycomb-shaped catalyst. There is a swinging perforated plate 18 in the powder bed under this honeycomb-shaped catalyst, The horizontal swinging motion averages the bulk density of the powder in the horizontal direction, prevents the occurrence of drift, and ensures the uniform contact of the gas with the powder and the catalyst.

After a predetermined residence time has passed in this fluidized bed, the powder overflows the weir 21 of the downcomer, enters the downcomer 20, and moves to the lower fluidized bed.

Magnesium hydroxide and magnesium carbonate in the inorganic powder absorb reaction heat and change to magnesium oxide in the methanation reactor. In the regeneration treatments of them, the inorganic powder containing magnesium oxide is reacted with water vapor to convert the magnesium oxide into magnesium hydroxide, and then the magnesium hydroxide is reacted with carbon dioxide to form magnesium carbonate.

FIG. 7 is a block flow diagram of this magnesium oxide regeneration process. The left side of this diagram is a block flow of the hydration reaction to form magnesium hydroxide from magnesium oxide, after cooling. The right side of this diagram is a block flow for carbonating a part or all of the magnesium hydroxide to form magnesium carbonate.

The magnesium oxide powder extracted from the methanation reactor 28 is cooled in the external powder cooler 11 and then returned to the methanation reactor 28 as magnesium hydroxide in the hydration reaction equipment 30. Further, when a part of this is to be made into magnesium carbonate, it is made into magnesium carbonate in the carbonation reaction device 31.

Here, the recycled ratio of the powder to be treated does not necessarily to be 100%.

In the three trail calculations in FIGS. 12-15, the ratio of magnesium hydroxide and magnesium carbonate in the powder is about 25 to 35% of the amount of inorganic powder added, and the remainder is inorganic powder not involving to the methanation (magnesium oxide, etc.). In other words, the regeneration of magnesium oxide can be performed by regenerating only the amount of magnesium hydroxide and magnesium carbonate required to offset the exothermic heat in the methanation reactor.

Therefore, in this block flow diagram, a portion of the magnesium oxide from the external powder cooler 11 and a portion of the magnesium hydroxide powder from the hydration reactor 30 are extracted and mixed with the treated powder to produce methane, then the mixed powder is transported to the chemical reactor 28.

FIG. 8 is a conceptual diagram in the case of using a moving bed as a regeneration treatment reactor for a chemical heat storage agent.

The powder extracted from the methanation reactor is once cooled by the external powder cooler, and then fed through powder transporting line 10 to the upper part of this regeneration reactor.

It is preferable to carry out the regeneration treatment of the inorganic powder using a moving bed capable of efficient countercurrent contact between the powder and the gas.

In case of using a moving bed to carry out regeneration treatment, when fine powder is used, or when the size of the apparatus is enlarged even if fine powder is not used, since drifting is tend to occur, it is preferable to use a moving bed having a swinging mechanism in order to suppress the generation of the drift and enable uniform regeneration of the inorganic heat storage agent.

In FIG. 8, the swinging perforated plates 18 and the heat transfer tubes 5 for heat removal in the moving bed are alternately installed in the height direction, rotational motion of the drive motor 16 is transmitted to the perforated swinging plate through the transmission shaft 17 to generate swinging motion. So, the powder bed is leveled in the horizontal direction to prevent the generation of the drift and enable uniform contact between the gas and the powder.

In the hydration reaction of magnesium oxide, since wet steam is preferable for the water vapor which is the reaction gas, this wet steam is dispersed and supplied into the moving bed from the air distributor 27 at the lower part so as to form a plug flow.

After the regeneration treatment, the powder is extracted from the lower part of the reactor and transported through the transport pipe 13 to the carbonation step or the methanation reactor via a storage tank.

In the carbonation reaction of magnesium hydroxide, carbon dioxide or flue gas, which is also a reaction gas, is supplied from the lower air distributor 27 so as to be uniformly dispersed in this moving bed.

Finally, the product gas coming out from the methanation reactor is unreacted carbon dioxide, hydrogen, and methane of 140° C. containing steam. Before storing this in the storage tank, it is cooled by the gas cooler 25 shown in FIG. 5 to condense the containing steam for separating and removing from the methane gas produced.

A small amount of contained unreacted carbon dioxide can be removed by a method such as chemical absorption with an aqueous solution of calcium hydroxide to convert into calcium carbonate, then methane containing about 1% of hydrogen can be obtained.

INDUSTRIAL APPLICABILITY

The present invention relates to a reactor for synthesizing methane using hydrogen and carbon dioxide. Carbon dioxide is a greenhouse gas, and its main source is boilers that burn fossil fuels such as coal, petroleum, and natural gas. It is preferable if hydrogen produced from renewable energy can cover the entire amount of energy from these fuels. However, hydrogen is highly explosive and must be stored at a fairly high pressure. There are great risks in using this as a general-purpose fuel. Therefore, if this hydrogen could be converted into methane and used, its safety and case of use will be greatly improved. Therefore, a highly efficient methanation reactor is desired.

As mentioned above, methane is excellent as a general-purpose fuel, but on the other hand, by converting hydrogen into methane, the amount of heat energy is reduced by about 17%.

If the heat generated in the methanation reactor would be released to the environment during heat removal, 17% of the heat energy possessed by hydrogen would be lost. If this heat could be stored and then the stored heat could be used effectively, all the thermal energy could be used effectively. For this purpose, it is preferable to use an inorganic powder containing magnesium hydroxide and magnesium carbonate, which are chemical heat storage agents, as a fluidizing medium and as heat removal method for reaction heat in a multi-stage fluidized bed used in a methanation reactor.

Also, when the carbon dioxide released by decarbonating this magnesium carbonate can be used as a raw material for methanation, this technology will become a CCUS technology that will fix the carbon dioxide as magnesium carbonate and use it more effectively.

As a concrete image, this CCUS technology can be used to fix carbon dioxide in flue gas from boilers of power plants, cement industry, steel industry, etc., which are large-scale sources of carbon dioxide as magnesium carbonate. This magnesium carbonate is transported to a hydrogen production facility, and methane can be used to synthesize from hydrogen and this magnesium carbonate in a methanation reactor in this facility. As the result, carbon recycling can be realized by using this methane or supplying it to others as fuel.

Currently, the mainstream of CCS technology for capturing carbon dioxide is the method using an amine-based absorbent, and naturally this carbon dioxide can be also used as the supplying source of the raw material for the methanation. However, carbon dioxide must be pressurized for its storage.

On the other hand, magnesium carbonate is considered advantageous in the point which can be stably stored for a long time under atmospheric pressure and is easy to transport as well.

With this technology, the magnesium carbonate powder is stored in a storage tank, and it is easy to take it out from the storage tank and transport it. This technology can be applied not only to the large-scale carbon dioxide generating sources described above, but also to a plurality of small-scale carbon dioxide generating sources that are separated from one another and dispersed.

Therefore, by converting the plurality of carbon dioxide generated in such small scale factories into magnesium carbonate, transporting them to the methanation reactor, gathering them, and storing them, carbon dioxides from these small distributed carbon dioxide sources can also be converted into methane.

This means that this technology is not necessarily limited to the boilers of large-scale power plants, but the plurality of carbon dioxide in the flue gas from small-scale factories in dispersed locations are fixed as magnesium carbonate and then transported to a facility with a methanation reactor, and they can be converted into methane.

It is undoubtedly important to catch and convert carbon dioxide from large-scale carbon dioxide sources, but ultimately, it is also necessary to catch and convert the carbon dioxide from small-scale carbon dioxide sources that are dispersedly located. The method of the present invention is also useful for such cases.

The heat and mass flow according to the invention was summarized in FIG. 9.

Combustion heat of hydrogen 968 MJ/kmol is converted into methane in the methanation reactor 28, and 165 MJ/kmol of the combustion heat is released by heat generation and reduced to 803 MJ/kmol. In this figure, the internal temperature of the methanation reactor is about 500° C. at the bottom and 200° C. at the top, but the temperature of the fluidized bed between them changes stepwise. By lowering the reaction temperature along with the progress of the gas reaction in this manner, the conversion ratio to methane at the outlet of the device can be increases.

By absorbing the heat generated by this reaction, magnesium hydroxide is dehydrated to magnesium oxide, and magnesium carbonate is decarbonated to magnesium oxide. That is, the generated magnesium oxide absorbs heat of 165 MJ/kmol and stores it.

Next, this magnesium oxide powder is transported to the regeneration processing facility 34 through the circulation loop 36 of the chemical heat storage agent by a means such as powder transportation. Here, since the reaction heat of 165 MJ/kmol absorbed in the methanation reactor is released when the magnesium oxide is regenerated, it can be recovered to use. This means that the heat generated in the methanation reactor is carried by the heat stream 37 to the regeneration facility where it is recovered to use it.

In this regeneration treatment facility, magnesium oxide is regenerated into magnesium hydroxide and magnesium carbonate, which are transported again to the methanation reactor via a circulation loop 36 for reuse. In this way, the magnesium-based chemical heat storage agent serves as a medium for transporting heat from the methanation reactor 28 to the regeneration treatment equipment 34, and as a transporting medium for carbon dioxide in the regeneration treatment equipment 34 to the methanation reactor 28. It circulates between both facilities. Here, when the powder agglomerates or pulverizes in the methanation reactor and the regeneration treatment device. In this circulation loop, a crushing or granulation process should be added to facilitate powder processing.

FIG. 10 illustrates the heat and material flow concept of FIG. 9 as flows between the methanation reactor and the regeneration reactor. The collected powder fixed carbon dioxide as magnesium carbonate from a plurality of factories 34 is transported to a methanation facility 28 which is storing hydrogen produced from renewable energy, where this magnesium carbonate and hydrogen supplying from the hydrogen producing facility 35 is used to produce methane. And it is stored in holder 29 of methane gas.

The magnesium oxide powder extracted from the methanation reaction equipment 28 is cooled to room temperature by the external powder cooler 11 and then stored in a storage tank 32 such as a silo. This magnesium oxide powder is returned to the carbon dioxide source plant 34, hydrated to magnesium hydroxide, and then regenerated as magnesium carbonate by absorbing carbon dioxide from the flue gas of the plants. Once magnesium hydroxide and magnesium carbonate stored in storage tank 33, it is transported to methanation reaction facility 28. In other words, the carbon dioxide in the flue gas of factories located far apart can be converted into methane by passing through the process of converting it into magnesium carbonate. On the other hand, in each factory 34, the thermal energy stored when hydrogen is converted into methane can be used by generating heat when regenerating to magnesium carbonate.

That is, according to this idea, the energy lost in converting hydrogen into methane can be recovered and used in other plants.

On the other hand, each factory provides carbon dioxide as magnesium carbonate in exchange for receiving this amount of heat. In addition, the exchange of energy between the methanation reaction facility and the carbon dioxide generation source can be independently operate of each other, even if the amount and timing of heat generation and demand were different, through heat storage agents, storage tanks, and transportation. It is also an advantage of the present invention.

From the calculation line in FIG. 1, it is considered that the carbonation reaction of magnesium hydroxide proceeds sufficiently even at around 140° C.

On the other hand, in the amine absorption method, it is necessary to cool down the temperature of the flue gas to 20 to 60° C. for absorbing carbon dioxide, but in the present invention, this cooling is not necessary. That is, carbon dioxide in flue gas is directly converted into magnesium carbonate without cooling. So, another advantage is that it does not affect the effective stack height.

Today, as measures against global warming, the reduction of carbon dioxide emissions and the promotion of the use of renewable energy are strongly appealed.

According to the present invention, in the case shown in FIG. 14, carbon dioxide extracted after burning fuel in a boiler is directly used, or in the case shown in FIG. 15, carbon dioxide is fixed as magnesium carbonate and use it. In either case, carbon dioxide can be converted into fuel methane using green hydrogen obtained from renewable energy and can be reused as a synthetic fuel. In other words, this is a CCUS technology that realizes complete carbon recycling and contributes to the drastic reduction of carbon dioxide emissions as a global warming countermeasure and the reduction of fossil resource usage.

CODE DESCRIPTION

1 Fluidized bed or moving bed apparatus
2 Fluidized bed or moving bed of powder
3 Reaction gas flow
4 Gas distribution plate
5 Heat transfer tube for cooling
6 Cooling medium (water, oil etc.)
7 lower stage of fluidized bed
8 Connecting pipe for reaction gas
9 Powder discharging part
10 Powder transporting line from the bottom of the reactor
11 External powder cooler
12 Moving bed
13 Powder transporting line
14 Multi-stage fluidized bed
15 Powder supply port to multi-stage fluidized bed
16 Driving motor for swinging mechanism
17 Driving shaft for swinging mechanism
18 Swinging perforated plate
19 Catalyst particles, honeycomb catalyst
20 Downcomer
21 Overflow weir of downcomer
22 Partition plate at the bottom of the downcomer
23 Raw material gas supplying port
24 Generated gas outlet
25 Generated gas cooler
26 Produced gas after cooling
27 Gas diffuser (gas spurger)
28 Methanation reactor
29 Generated methane holder
30 Hydration reactor 31 Carbonation reactor
32 Magnesium oxide storage tank
33 Powder storage tank after regeneration treatment
34 factory (hydration reaction facility+carbon dioxide source)
35 Hydrogen production plant
36 Circulation loop of chemical heat storage agent
37 Flow of absorbed reaction heat

The invention claimed is:

1. A method for producing methane by reacting carbon dioxide and hydrogen in the presence of a catalyst, a tower type reactor in which multiple stages of powder beds are arranged vertically, comprising:

preparing a reactor in which each powder bed contains at least one inorganic powder selected from the group consisting of sand, silica, magnesia, alumina and calcia and the catalyst;

introducing a reaction mixture gas containing carbon dioxide and hydrogen into the space below the lowermost powder bed in the reactor;

passing, sequentially through the ascending flow of the reaction mixture, gas from the lowest powder bed to the uppermost powder bed to form a multi-stage fluidized bed;

extracting a product gas containing methane produced by contacting the reaction mixture gas with the catalyst arranged in each powder bed from the space above the uppermost powder bed;

supplying, continuously, the inorganic powder to the uppermost powder bed;

causing the inorganic powder in each stage of the powder bed to continuously flow down to the adjacent lower powder bed, by:

discharging, continuously, the inorganic powder from the lowermost powder bed, while maintaining the amount of the inorganic powder in each powder bed constant; and forming a downward flow of the inorganic powder that flows down in the reactor through the plurality of stages of powder beds in sequence, in the reactor, the ascending flow of the reaction mixture gas and the downward flow of the inorganic powder are in countercurrent contact;

constructing a continuous multi-stage fluidized bed reactor having a temperature gradient in which the temperature of the plurality of powder beds decreases sequentially from the lowest powder bed to the uppermost powder bed;

adjusting the cooling amount of the inorganic powder so that the temperature of the inorganic powder supplied to the uppermost powder bed is in the range of 100 to 300° C.; and adjusting the circulation amount of the inorganic powder so that the temperature of the inorganic powder extracted from the lowermost powder bed is in the range of 300 to 600° C., wherein:

the inorganic powder fed to the uppermost powder bed contains magnesium hydroxide, magnesium carbonate or a mixture thereof;

the inorganic powder extracted from the lowermost powder bed contains magnesium oxide produced by dehydration of the magnesium hydroxide or decarbonation of magnesium carbonate, or a mixture thereof and unreacted inorganic powder in the reactor; and the inorganic powder extracted from the lowermost powder bed is cooled in an atmosphere in which water vapor or carbon dioxide is contained, thereby converting magnesium oxide contained in the inorganic powder into magnesium hydroxide or magnesium carbonate.

2. The method according to claim 1, wherein:

the inorganic powder extracted from the lowermost powder bed is first brought into contact with water vapor to convert at least part of the magnesium oxide in the inorganic powder into magnesium hydroxide; and the inorganic powder is brought into contact with carbon dioxide to convert at least a portion of the magnesium hydroxide in the inorganic powder into magnesium carbonate.

3. The method according to claim 2, wherein:

the catalyst is held in each stage of the powder bed in such a manner that the catalyst does not circulate with the inorganic powder and stays in the powder bed; and different catalysts are used in the powder bed at the lower stage where the temperature of the inorganic powder is above 300° C. and in the powder bed at the upper stage where the temperature of the inorganic powder is below 300° C., respectively.

4. The method according to claim 3, wherein the catalyst used in the lower stage powder bed comprises nickel and the catalyst used in the upper stage powder bed comprises ruthenium.

5. The method according to claim 2, wherein the reactor comprises a swinging mechanism capable of swinging the powder beds of the multiple stages.

6. The method according to claim 1, wherein the inorganic powder fed to the uppermost powder bed contains magnesium carbonate, further comprising:

adjusting the circulation amount of the inorganic powder so that the temperature of the inorganic powder extracted from the lowermost powder bed is 400° C. to 500° C.; and using a mixed gas containing a flue gas and a hydrogen as the reaction mixed gas.

7. The method according to claim 6, wherein:

the catalyst is held in each stage of the powder bed in such a manner that the catalyst does not circulate with the inorganic powder and stays in the powder bed; and different catalysts are used in the powder bed at the lower stage where the temperature of the inorganic powder is above 300° C. and in the powder bed at the upper stage where the temperature of the inorganic powder is below 300° C., respectively.

8. The method according to claim 7, wherein the catalyst used in the lower stage powder bed comprises nickel and the catalyst used in the upper stage powder bed comprises ruthenium.

9. The method according to claim 6, wherein the reactor comprises a swinging mechanism capable of swinging the powder beds of the multiple stages.

10. The method according to claim 1, wherein the inorganic powder fed to the uppermost powder bed contains magnesium carbonate, further comprising:

adjusting the circulation amount of the inorganic powder so that the temperature of the inorganic powder extracted from the lowermost powder bed is 400° C. to 500° C.; and converting magnesium oxide included in the inorganic powder is converted into magnesium carbonate by contacting the inorganic powder extracted from the lowermost powder bed with flue gas containing carbon dioxide.

11. The method according to claim 10, wherein:

the catalyst is held in each stage of the powder bed in such a manner that the catalyst does not circulate with the inorganic powder and stays in the powder bed; and different catalysts are used in the powder bed at the lower stage where the temperature of the inorganic powder is above 300° C. and in the powder bed at the upper stage where the temperature of the inorganic powder is below 300° C., respectively.

12. The method according to claim 11, wherein the catalyst used in the lower stage powder bed comprises nickel and the catalyst used in the upper stage powder bed comprises ruthenium.

13. The method according to claim 10, wherein the reactor comprises a swinging mechanism capable of swinging the powder beds of the multiple stages.

14. The method according to claim 1, wherein;

the catalyst is held in each stage of the powder bed in such a manner that the catalyst does not circulate with the inorganic powder and stays in the powder bed; and different catalysts are used in the powder bed at the lower stage where the temperature of the inorganic powder is above 300° C. and in the powder bed at the upper stage where the temperature of the inorganic powder is below 300° C., respectively.

15. The method according to claim 14, wherein the catalyst used in the lower stage powder bed comprises nickel and the catalyst used in the upper stage powder bed comprises ruthenium.

16. The method according to claim 15, wherein the reactor comprises a swinging mechanism capable of swinging the powder beds of the multiple stages.

17. The method according to claim 14, wherein the reactor comprises a swinging mechanism capable of swinging the powder beds of the multiple stages.

18. The method according to claim 1, wherein the reactor comprises a swinging mechanism capable of swinging the powder beds of the multiple stages.

* * * * *